(12) United States Patent
Smaldone et al.

(10) Patent No.: US 8,105,571 B2
(45) Date of Patent: *Jan. 31, 2012

(54) METHOD OF TREATING PULMONARY DISEASE WITH INTERFERONS

(75) Inventors: Gerald Smaldone, Setauket, NY (US); Rany Condos, Beechurst, NY (US)

(73) Assignees: New York University, New York, NY (US); The Research Foundation of the State University of New York, Stony Brook, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/460,376

(22) Filed: Jul. 17, 2009

(65) Prior Publication Data

US 2010/0015062 A1 Jan. 21, 2010

(51) Int. Cl.
*A61K 38/00* (2006.01)
*A61K 38/21* (2006.01)
*C07K 14/00* (2006.01)

(52) U.S. Cl. .......... 424/85.4; 514/1.6; 514/1.7; 514/2.4; 514/1.5; 424/85.5; 430/351

(58) Field of Classification Search ........................ None
See application file for complete search history.

(56) References Cited

U.S. PATENT DOCUMENTS

| | | | | |
|---|---|---|---|---|
| 6,964,761 | B1 * | 11/2005 | Condos et al. | 424/85.5 |
| 2001/0043906 | A1 * | 11/2001 | Vlasselaer et al. | 424/43 |

FOREIGN PATENT DOCUMENTS

| | | |
|---|---|---|
| CN | 1151168 A | 6/1997 |
| CN | 1569225 A | 1/2005 |
| WO | 01/49260 | 7/2001 |
| WO | 2004/112691 | 12/2004 |
| WO | 2004/112691 A2 | 12/2004 |

OTHER PUBLICATIONS

Brusselle et al., Am J Respir Cell Mol Biol , Mar. 1995; 12(3):254-259.
Coyle et al., Am J Respir Cell Mol Biol Jul. 1995; 13(1):54-59.
Pretolani et al., Res Immunol Jan. 1997.
Borish, L et al., J Allergy Clin Immunol Jun. 1996 97(6):1288-1296.
Koning et al., Cytokine Jun. 1997; 9(6):427-436.
Zuany-Amorim et al., J Clin Invest 1996:2644-2651.
Zuany-Amorim et al., J Immunol Jul. 1, 1996; 157(1):377-84).
Ohkawara et al., Am J Respir Cell Mol Biol May 1997; 16(5):510-20.
Kips et al., Am J Respir Crit Care Med Feb. 1996; 153(2):535-9.
Brusselle et al., Am J Respir Cell Mol Biol Dec. 1997; 17(6):767-71.
Hogan et al.,—Eur J Immunol Feb. 1998; 28(2):413-23.
Imada et al., (1995) Immunology 85(3): 373-80.
Corrigan et al., (1990) Am Rev Respir Dis 141(4) Pt 1: 970-7.
Leonard et al., (1997) Am J Respir Cell Mol Biol 17( 3): 368-75.
Kang et al., (1997) J Interferon Cytokine Res 17(8): 481-7).
Bemiller et al. (1995) Blood Cells Mol Dis 21(3): 239-47.
Weening et al., (1995) Eur J Pediatr 154(4): 295-8.
Boguniewicz et al., (1995) J Allergy Clin Immunol 95(1) Pt 1: 133-5.
Condos et al., (1997) Lancet 349(9064): 1513-5.
Nicholson, Histopathology, 2002, 41, 381-391; White, J Pathol 2003, 201, 343-354.
King et al., 2000, Am J of Resp. and Critical Care Med., 164, 1025-1032.
Mapel et al. (1996) Chest 110:1058-1067.
Raghu et al. (1991) Am. Rev. Respir. Dis. 144:291-296.
Jaffe et al., J Clin Invest. 88, 297-302 (1991).
Ziesche et al., (1999) N. Eng. J. Med., 341, 1264-1269.
Adjei et al., Pharmaceutical Research, vol. 7, No. 6, pp. 565-569 (1990).
Adjei et al., International Journal of Pharmaceutics, 63:135-144 (1990).
Braquet et al., Journal of Cardiovascular Pharmacology, vol. 13, suppl. 5, s. 143-146 (1989).
Hubbard et al., Annals of Internal Medicine, vol. III, No. 3, pp. 206-212(1989).
Smith et al., J. Clin. Invest., vol. 84, pp. 1145-1146 (1989).
Pine et al., (1990) Mol Cell Biol 10(6): 2448-57.
White, J Pathol 2003, 201, 343-354.
Oswein et al., "Aerosolization of Proteins", Proceedings of Symposium on Respiratory Drug Delivery II, Keystone, Colorado, Mar. 1990.
Condos et al., (1998) Am J Respir Crit Care Med 157(3): A187.
Strieter et al., Am J Respir Crit Care Med. (2004).
Vilcek et al., (1994) Int Arch Allergy Immunol 104(4): 311-6.
Young et al., (1995) J Leukoc Biol 58(4): 373-81.
Pine, R (1992) J Virol 66(7): 4470-8.
Pine et al., (1994) Embo J 13(1): 158-67.
Harada et al., (1994) Mol Cell Biol 14(2): 1500-9.
Johnson et al., (1994) Mol Cell Biol 14(2): 1322-32.
White et al., (1996) Immunity 5(4): 365-76.
Nunokawa et al., (1994) Biochem Biophys Rees Commun 200(2): 802-7.
Darnell (1996) Recent Prog Horm Res 51:391-403.
Ivashkiv, LB (1995) Immunity 3(1):1-4.
Raghu et al., (1989) Am. Rev. Resp. Dis. 140:95-100. Condos et al., Chest (2004); 125:2146-2155.
Erbes et al., Chest (1997); 111: 51-57.
David et al., (1995) Science 269(5231):1721-3.
Wen, Z et al., (1995) Cell 82(2): 241-50.
Cho et al., (1996) J Immunol 157(11): 4781-9.
David et al., (1996) J Biol Chem 271(27): 15862-5.
Gupta et al., (1995) Science 267(5196): 389-93.
Hibi et al., (1993) Genes Dev 7(11): 2135-48.
Parker et al., (1996) Mol Cell Biol 16(2):694-703.
Schindler et al., (1992) Science 257(5071): 809-13.
Shuai et al., (1992) Science 258(5089): 1808-12.
Carlesso et al., (1996) J Exp Med 183(3): 811-20.
Gouilleux-Gruart et al., (1996) Blood 87(5): 1692-7.
Gilmour et al., (1995) Proc Nati Acad Sci USA 92(23): 10772-6.
Demedts et al., N. Engl J Med 2005; 353:21.
Raghu et al., Am J. Resp Crit Care Med (2008); 178: 948-955.
Kanazawa, et al., Chest, (2003) 123:2; 600-603.
Raghu, et al., New England Journal of Medicine (2004); 350:2: 125-133.
Simon, et al., Allergy 2003 58: 1250-1255.
Liu, et al., Clin J. Pharmacoepidemiol 2004 13(5):230-231.

\* cited by examiner

*Primary Examiner* — Christine J Saoud
*Assistant Examiner* — Jegatheesan Seharaseyon
(74) *Attorney, Agent, or Firm* — Klauber & Jackson LLC

(57) ABSTRACT

A method of treating a pulmonary disease such as, for instance idiopathic pulmonary fibrosis (IPF), mixed connective tissue disease and asthma, comprising administering an aerosolized interferon such as interferon γ in a therapeutically effective amount is provided herein. Also, pharmaceutical compositions of one or more aerosolized interferon(s) alone or in combination with other therapeutic agents are provided.

20 Claims, 14 Drawing Sheets

(filled bar indicates aerosol generation)

SLOW & DEEP
following 3 breaths of Test aerosol (albuterol)

TIDAL BREATHING
following 20 breaths of Test aerosol (albuterol)

FIG. 5

INF-γ deposited in lung = 54μg;
sC/P = 1.28, consistent with
peripheral deposition

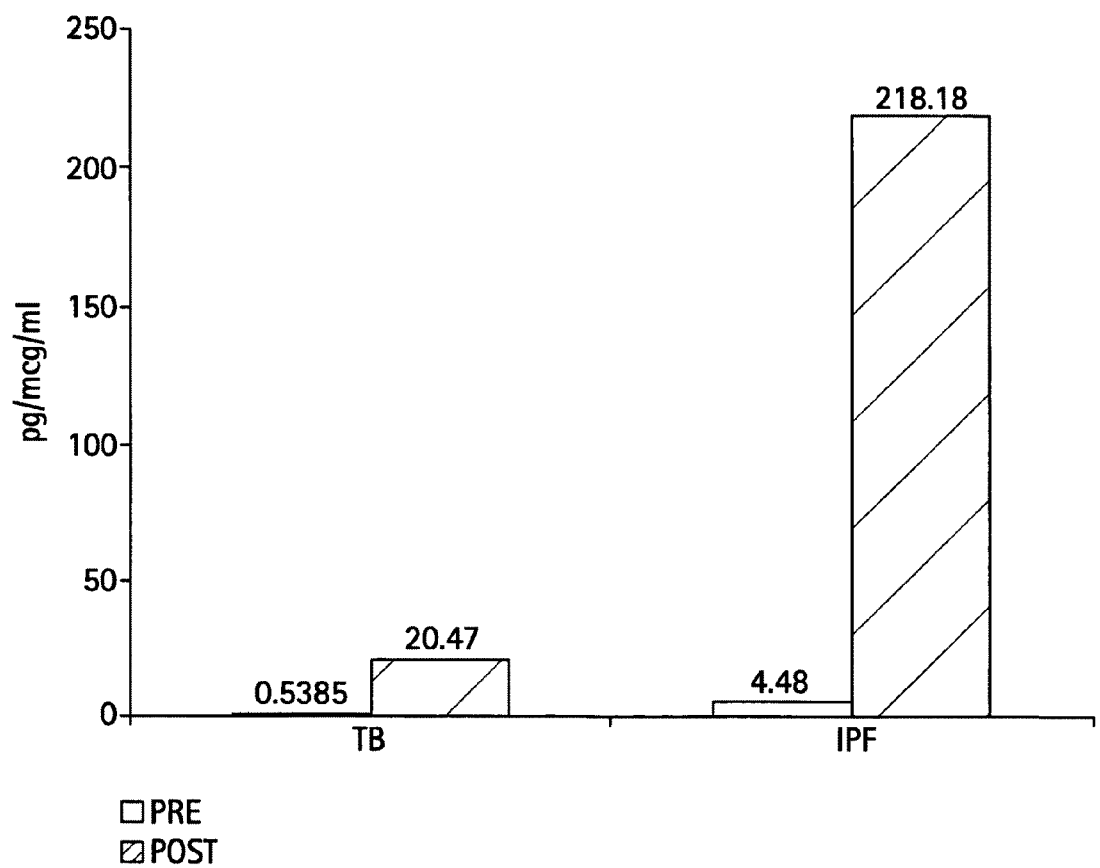

FIG. 11

% change in peak flow after treatment with aerosol IFN γ

- □ Ni
- ◇ Cyr
- ○ Wu
- △ Alcantara
- ⊞ Lin
- ◆ Zheng
- ⊕ Ellis

FIG. 13
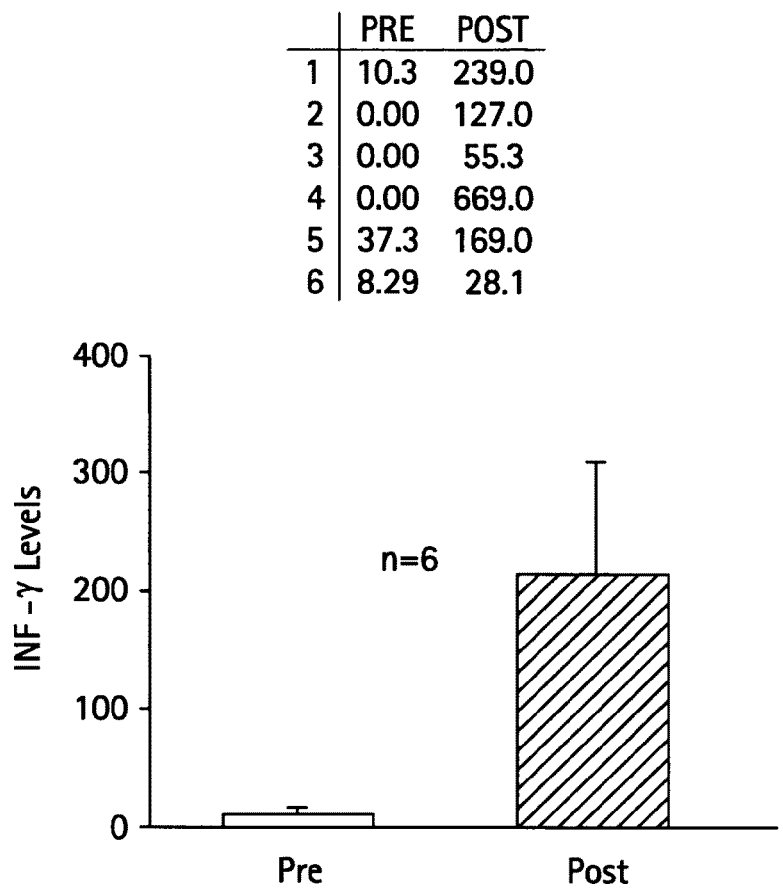
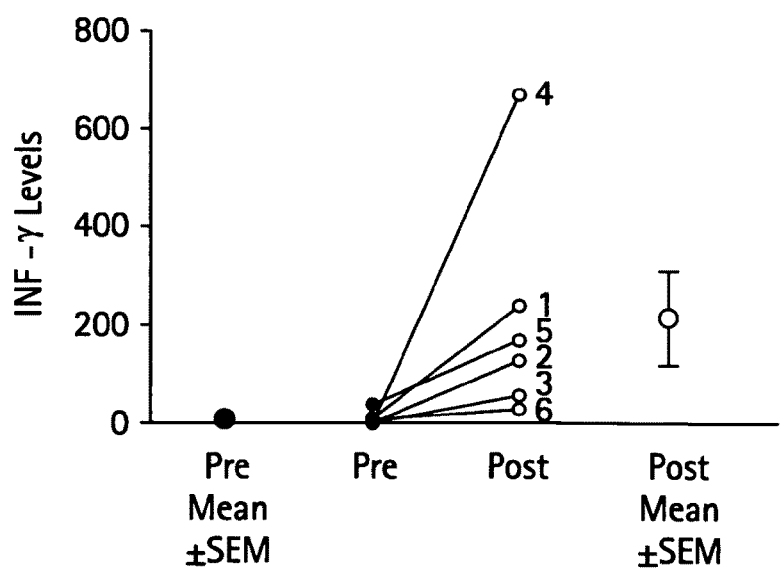

FIG. 14
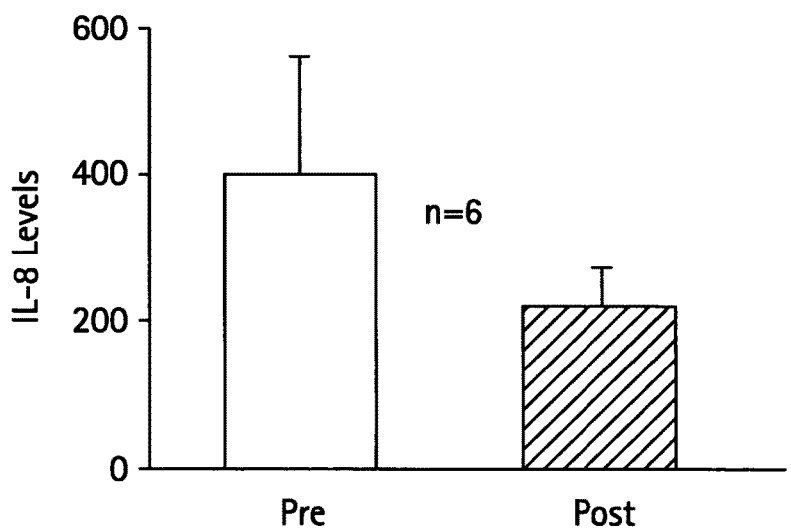
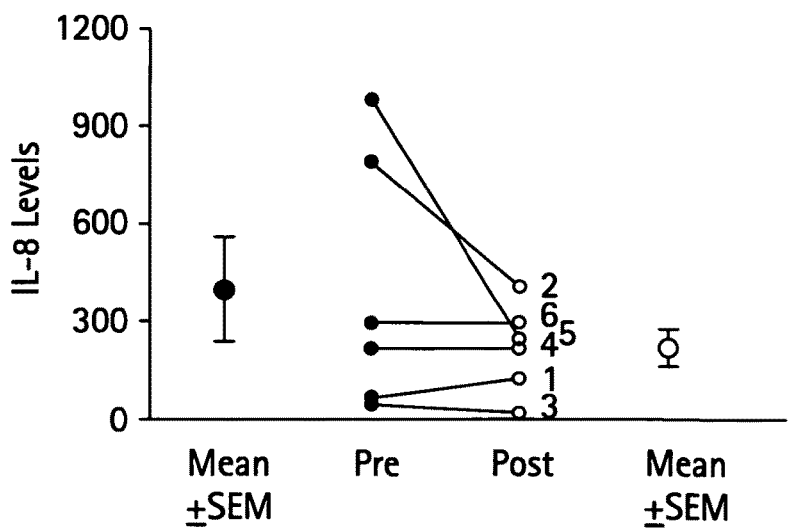

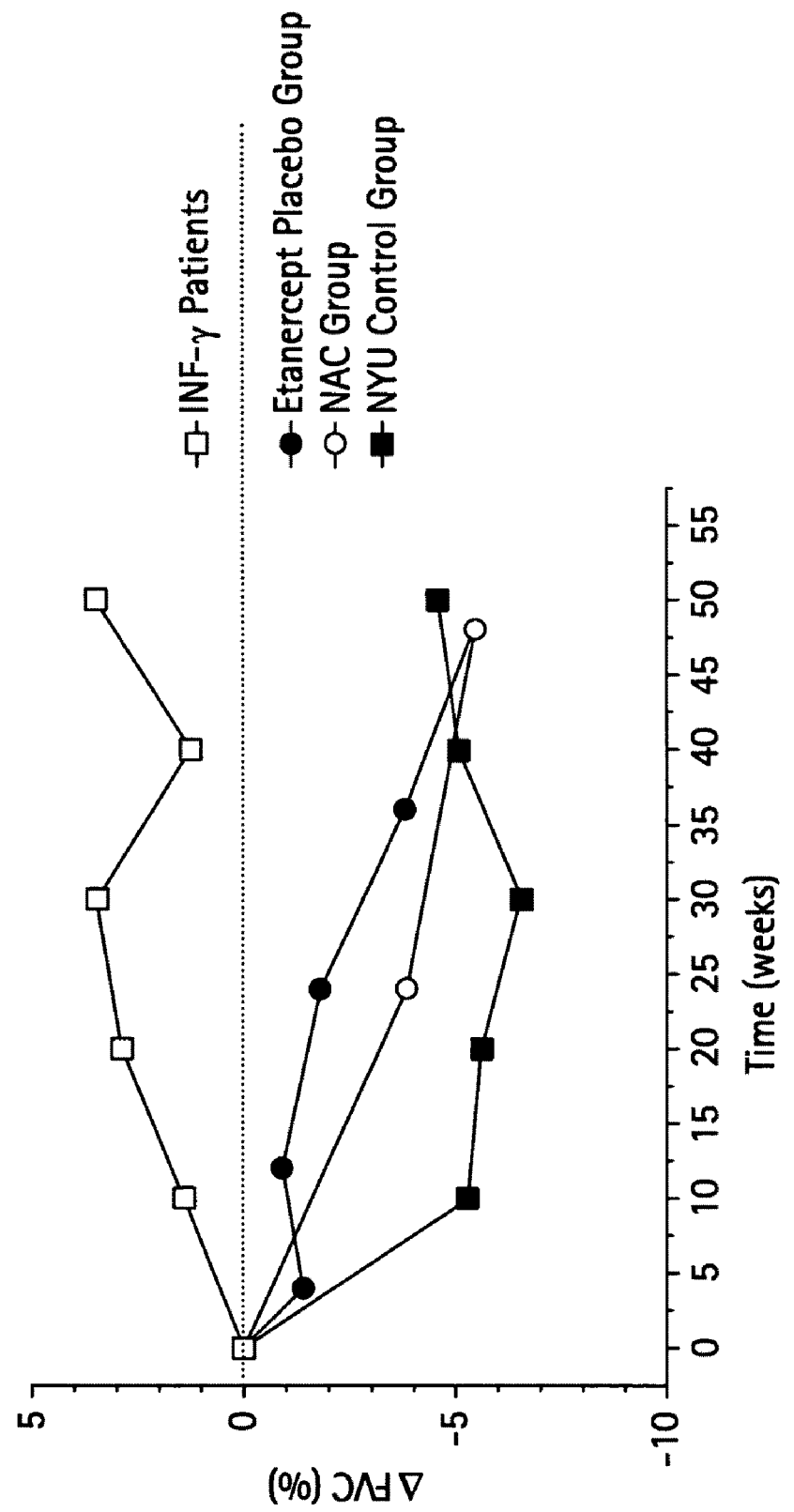

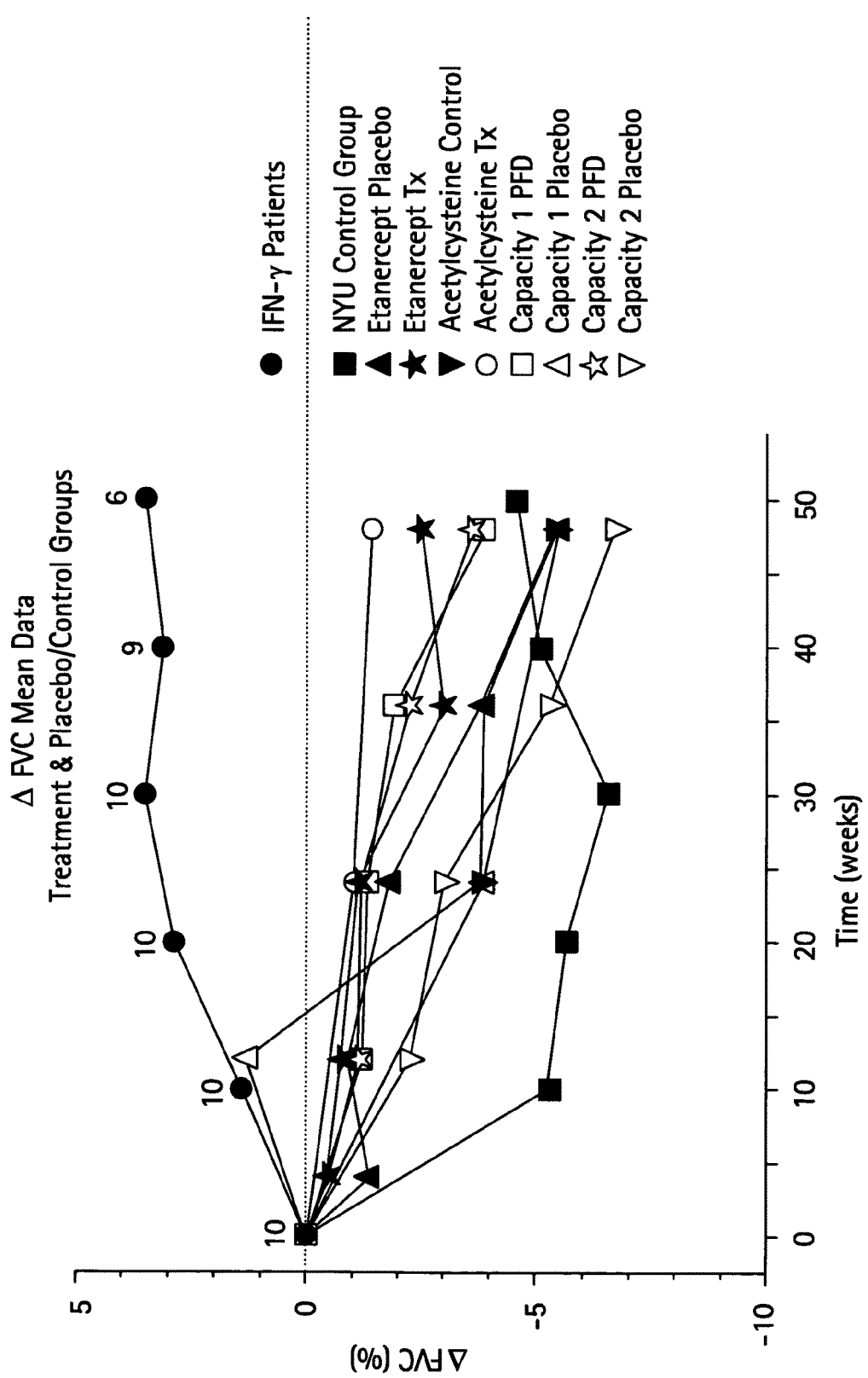

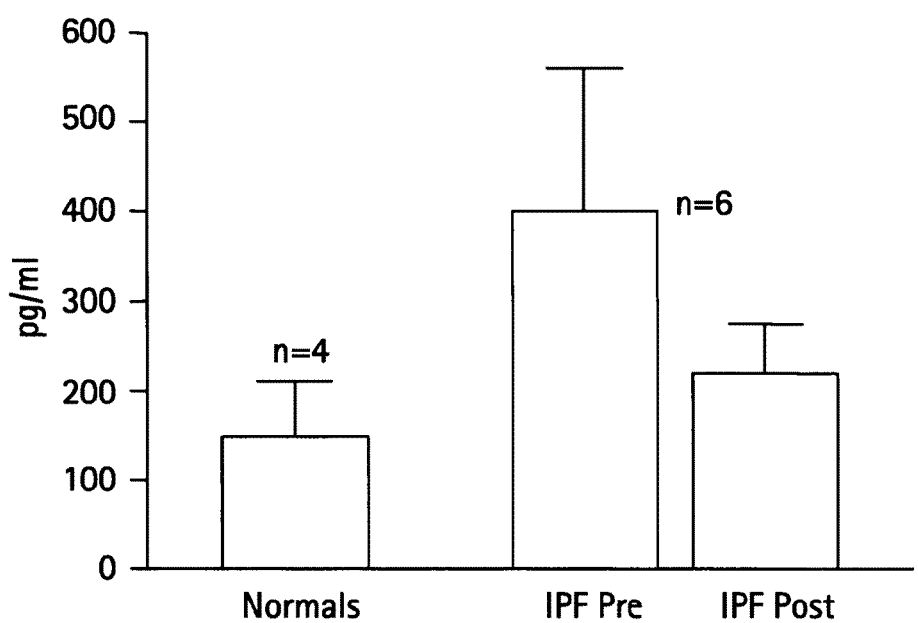
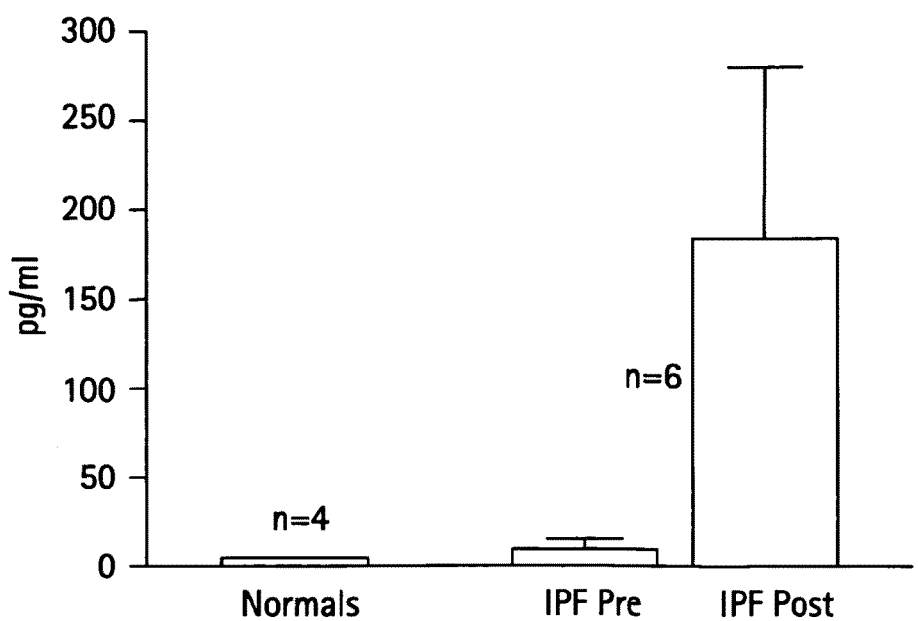

ically children. Furthermore, others have demonstrated
METHOD OF TREATING PULMONARY DISEASE WITH INTERFERONS

GOVERNMENT SUPPORT

Some research leading to the present invention was supported in part by research NIH grant R01 HL55791, K07 HL03030, and M01 RR00096. The government may have certain rights in the present invention.

This application is continuation in part of U.S. Ser. No. 12/322,440, filed Feb. 3, 2009 which is a division of U.S. Ser. No. 11/231,322, filed Sep. 20, 2005.

FIELD OF THE INVENTION

This invention relates to methods of treating pulmonary diseases using aerosol interferons, formulations of one or more interferons for aerosol delivery and methods for determining aerosol deposition.

BACKGROUND

The mainstay of asthma treatment according to current NAEPP/NIH guidelines remains anti-inflammatory agents, of which corticosteroids are the most potent. However, long term administration of corticosteroids is associated with systemic side effects. Furthermore, some asthmatics are resistant to corticosteroids. Therefore, there is a need for new agents aimed at the inflammatory response in allergic airway disease.

The immune mechanism of asthma involves the polarized involvement of memory CD4+ T-helper cell with an imbalance of cells secreting type 2 (Th2) cytokines (interleukin (IL)-4, IL-5). The cytokine interferon-γ (INF-γ) is required for naive CD4+ lymphocyte differentiation to Th1 phenotype.

Airways inflammation in asthma is characterized by the presence of an increased number of eosinophils and activated CD4+ T cells. Asthma involves the polarized involvement of memory CD4+ T helper cells with an imbalance of cells secreting Th2-type cytokines over those secreting Th1-type cytokines. There is increased production of a number of cytokines including Type 2 cytokines IL-4 and IL-5, tumor necrosis factor (TNF-α), and granulocyte-macrophage colony-stimulating factor (GM-CSF) as well as tissue eosinophilia and increased IgE production. Most studies of cytokine profiles in airway inflammation come from the murine model of asthma. Animals are sensitized and challenged with antigen, usually ovalbumin and are found to have antigen specific IgE production, airway eosinophilia and airway hyperresponsiveness to aerosol antigen challenge. These changes are associated with increased Th2 cytokines and decreased INF-γ production (Brusselle et al., *Am J Respir Cell Mol Biol*, 1995 Mar; 12(3):254-259).

The Th2 cytokine IL-4 plays a prominent role in airway inflammation by promoting isotype switching of B cells to IgE synthesis and inducing naive T cell differentiation to Th2 lymphocytes. IL-4 knockout mice challenged with aerosolized antigen failed to produce specific IgE, airway hyperresponsiveness, airway eosinophilia, or Th2 cytokines in the airways (Brusselle et al., *Am J Respir Cell Mol Biol*, 1995 March; 12(3):254-259.) Wild-type mice treated with anti-IL-4 during the initial exposure to antigen but not during challenge inhibited IL-5 production and airways eosinophilia, whereas anti-IL-4 given during antigen challenge did not inhibit airways eosinophilia, indicating that IL-4 is essential for the induction of a local Th2 response (Coyle et al., *Am J Respir Cell Mol Biol* 1995 July; 13(1):54-59).

IL-10 is a cytokine produced by Th1 and Th2 lymphocytes, monocytes and macrophages, mast cells, keratinocytes, and eosinophils. IL-10 acts as an anti-inflammatory cytokine by downregulating the synthesis of proinflammatory cytokines by different cells, particularly monocytic cells. IL-10 downregulates the production of IL-5 by functionally inhibiting antigen presenting cells (APC) (Pretolani et al.,*Res Immunol* 1997 Jan.). A direct effect of IL-10 on eosinophil function has been demonstrated as well. Low concentrations of IL-10 were almost as active as corticosteroids in decreasing CD4 expression on eosinophils and accelerating cell death. GM-CSF is a cytokine directly involved in the homing and activation of eosinophils and neutrophils in inflamed tissues. Diminished levels of IL-10 production by PBMC and alveolar macrophages have been noted in asthmatic patients compared to normal controls (Borish, L et al., *J Allergy Clin Immunol* 1996 Jun.; 97(6):1288-1296; Koning et al., *Cytokine* 1997 Jun; 9(6):427-436). In two models of allergic inflammation in mice, instillation of IL-10 protected sensitized mice from airway eosinophilia and neutrophilia possibly by inhibiting IL-5 and TNF-α(Zuany-Amorim et al., J Clin Invest 1996: 2644-2651; Zuany-Amorim et al., *J Immunol* 1996 Jul 1; 157(1):377-84).

Consistent with the Th2/Th1 dichotomy of cytokine production, murine models of asthma observe a cytokine profile of IL-4 and IL-5 predominance and low levels of the Th1 cytokines INF-γ and IL-12 (Ohkawara et al., *Am J Respir Cell Mol Biol* 1997 May; 16(5):510-20). Recent animal studies look at treatment with recombinant murine IL-12 in an attempt to reverse Th2 predominance. In vitro data indicate that the presence of IL-12 during the primary antigen stimulation of T-lymphocytes favors the development of Th1 cells (Kips et al., *Am J Respir Crit Care Med* 1996 Febuary; 153 (2):535-9). Kips confirmed this in vivo by administering IL-12 at the time of immunization and preventing production of specific IgE, airway eosinophilia, and airway hyperreactivity. Although, IL-12 administration during the aerosol challenge of already sensitized mice prevented airway eosinophilia and airway hyperresponsiveness, it did not decrease specific IgE production, suggesting that IL-12 stimulates the differentiation of naive Th cells into Th1 cells, and can suppress the development of Th2 cells. Inhibition of antigen induced airway eosinophilia by IL-12 is INF-γ dependent during the initial sensitization, but becomes INF-γ independent during the secondary challenge (Brusselle et al., *Am J Respir Cell Mol Biol* 1997 December; 17(6):767-71). In addition, mucosal gene transfer of IL-12 gene in the lung via vaccinia virus vector to sensitized mice prior to aeroallergen challenge has been demonstrated to lead to suppression of IL-4, IL-5, airway hyperresponsiveness, and airway eosinophilia in an INF-γ dependent manner (Hogan et al.,—*Eur J Immunol* 1998 Febuary; 28(2):413-23).

Increasing INF-γ levels may drive the immune response to a Th1 phenotype and may be beneficial in asthma. Clinical correlation in humans has focused on cytokine levels in serum or stimulated PBMC. Most measurements of cytokines using stimulated PBMC have been performed in children. These studies have demonstrated an increased propensity towards IL-4 and IL-5 production and decreased production of INF-γ is asthmatic children. Furthermore, others have demonstrated an inverse association between atopy and/or asthma severity and release of INF-γ (Imada et al., (1995) *Immunology* 85(3): 373-80; Corrigan et al., (1990) *Am Rev Respir Dis* 141(4) Pt 1: 970-7; Leonard et al., (1997) *Am J Respir Cell Mol Biol* 17(3): 368-75; Kang et al., (1997) *J Interferon Cytokine Res* 17(8): 481-7). Cytokine levels in BAL fluid from asthmatic patients reveal low levels of INF-γ (Kang et al., (1997) *J Interferon Cytokine Res* 17(8): 481-7).

Clinical trials of rINF-γ in humans are few. As of 1999, INF-γ is indicated for the treatment of chronic granulomatous disease in which prolonged treatment (average duration 2.5 years) was associated with improvement in skin lesions, with minimal adverse events (fever, diarrhea, and flu-like illness) (*N Engl J Med* 324 (8):509-16; Bemiller et al. (1995) *Blood Cells Mol Dis* 21(3): 239-47; Weening et al., (1995) *Eur J Pediatr* 154(4): 295-8). Boguniewicz treated 5 patients with mild atopic asthma with escalating doses of aerosolized r INF-γ (maximum dose of 500 mcg, total study dose of 2400 mcg) delivered over 20 days (Boguniewicz et al., (1995) *J Allergy Clin Immunol* 95(1) Pt 1: 133-5). All patients tolerated the nebulized r INF-γ but there were no significant changes in the endpoints evaluated which included peak flow.

Nebulized r INF-γ was administered to 5 patients with persistent acid fast bacilli (AFB) smear and culture positive multiple-drug resistant tuberculosis (TB) (Condos et al., (1997) *Lancet* 349(9064): 1513-5). Patients received aerosol r INF-γ, 500 mcg, 3 times weekly for 4 weeks (total study dose 6000 mcg). Therapy was tolerated well with minimal side effects. At the end of the 4 weeks, 4 of the 5 patients were sputum AFB-smear negative and the time to positive culture increased indicating a reduced organism load after treatment. Interestingly, in these reported and in additional patients, PEFR performed 1 hour after treatment improved by 6% (n=10).

The idiopathic interstitial pneumonias have been grouped into seven categories based upon histology. They include usual interstitial pneumonia (UIP), non-specific interstitial pneumonia (NSIP), diffuse alveolar damage (DAD), organizing pneumonia (OP), desquamative interstitial pneumonia (DIP), respiratory bronchiolitis (RB), and lymphocytic interstitial pneumonia (LIP). See, e.g. Nicholson, *Histopathology*, 2002, 41, 381-391; White, *J Pathol* 2003, 201, 343-354.

The term "idiopathic pulmonary fibrosis" (IPF), synonymous with "cryptogenic fibrosing alveolitis" (CFA) is the clinical term for a major subgroup of the idiopathic interstitial pneumonias, and it describes a disease characterized by idiopathic progressive interstitial disease with a mean survival from the onset of dyspnea of 3 to 6 years. A diagnosis of idiopathic pulmonary fibrosis is made by identifying usual interstitial pneumonia (UIP) on lung biopsy. The histological pattern is characterized by heterogeneity that includes patchy chronic inflammation (alveolitis), progressive injury (small aggregates of proliferating myofibroblasts and fibroblasts, termed fibroblastic foci) and fibrosis (dense collagen and honeycomb change). (See, e.g. King et al., 2000, *Am J of Resp. and Critical Care Med.*, 164, 1025-1032). Treatment of another subgroup of interstitial pneumonia is not predictive of successful therapy for idiopathic interstitial fibrosis.

Corticosteroids and cytotoxic agents have been a mainstay of therapy, with only 10-30% of patients showing an initial transient response, suggesting the need for long-term therapy (Mapel et al. (1996) *Chest* 110: 1058-1067; Raghu et al. (1991) *Am. Rev. Respir. Dis.* 144:291-296). Due to the poor prognosis of patients with idiopathic pulmonary fibrosis, new therapeutic approaches are needed.

Interferons are a family of naturally-occurring proteins that are produced by cells of the immune system. Three classes of interferons have been identified, alpha, beta and gamma. Each class has different effects though their activities overlap. Together, the interferons direct the immune system's attack on viruses, bacteria, tumors and other foreign substances that may invade the body. Once interferons have detected and attacked a foreign substance, they alter it by slowing, blocking, or changing its growth or function.

Interferon-γ is a pleiotropic cytokine that has specific immune-modulating effects, e.g. activation of macrophages, enhanced release of oxygen radicals, microbial killing, enhanced expression of MHC Class II molecules, anti-viral effects, induction of the inducible nitric oxide synthase gene and release of NO, chemotactic factors to recruit and activate immune effector cells, down regulation of transferrin receptors limiting microbial access to iron necessary for survival of intracellular pathogens, etc. Genetically engineered mice that lack interferon-γ or its receptor are extremely susceptible to mycobacterial infection.

Recombinant INF-γ was administered to normal volunteers and cancer patients in the 1980s through intramuscular and subcutaneous routes. There was evidence of monocyte activation, e.g. release of oxidants. Jaffe et al. reported rINFγ administration to 20 normal volunteers. (See, Jaffe et al., *J Clin Invest.* 88, 297-302 (1991)) First, they gave rINF-γ 250 µg subcutaneously noting peak serum levels at 4 hours and a trough at 24 hours.

Several clinical trials were sponsored to evaluate INF-γ for infectious diseases. The MDR-TB clinical trial, entitled "A Phase II/III Study of the Safety and Efficacy of Inhaled Aerosolized Recombinant Interferon-γ 1 b in Patients with Pulmonary Multiple Drug Resistant Tuberculosis (MDR-TB) Who have Failed an Appropriate Three Month Treatment," enrolled 80 MDR-TB patients at several sites (Cape Town, Port Elizabeth, Durban, Mexico) and randomized them to receive aerosol rINF-γ (500 µg MWF) or placebo for at least 6 months in addition to second line therapy. This clinical trial was stopped prematurely due to lack of efficacy on sputum smears, M tb culture, or chest radiograph changes.

Ziesche et al. gave rINF-γ subcutaneously at a dose of 200 mg three times a week in addition to oral prednisone to 9/18 patients with idiopathic pulmonary fibrosis (IPF). See, Ziesche et al., (1999) *N. Eng. J. Med.*, 341, 1264-1269). The results of a subsequent phase 3 clinical trial of interferon γ-1b therapy for IPF were recently published. Although this was the first clinical trial of IPF that had an adequate sample size and was a randomized, prospective, double-blind, placebo-controlled study, no significant effect on markers of physiologic function, such as forced vital capacity, was observed. However, more deaths occurred in the placebo group, and survival was significantly better for a subset of patients who received interferon γ-1b therapy and had a forced vital capacity of 55% or greater and diffuse lung capacity for carbon monoxide of 35% or greater of the normal predicted values. The discordance between disease progression and survival in that study remains to be explained. One possibility is that interferon γ-1b therapy improves host defense against infection and diminishes the severity of lower respiratory tract infection when it complicates the clinical course of patients with IPF. This possibility is supported by the observation by Strieter et al. that the interferon-inducible CXC chemokine, I-TAC/CXCL11, which has antimicrobial properties, was significantly up-regulated in plasma and bronchoalveolar lavage (BAL) fluid in individuals who received interferon γ-1b compared to those who received placebo, whereas profibrogenic cytokines were generally not significantly altered by interferon γ-1b therapy over a 6-month treatment period. (See, Strieter et al., *Am J Respir Crit Care Med.* (2004). One possibility to explain the lackluster results is inadequate levels of drug delivered to the lung interstitium with current dosing strategies.

BRIEF SUMMARY OF THE INVENTION

In one aspect, the present invention features a method of treating a pulmonary disease in a subject suffering from a pulmonary disease, comprising administering an aerosolized interferon in a therapeutically effective amount. In many embodiments, the pulmonary disease is an obstructive pulmonary disease. In some embodiments the pulmonary disease is asthma or idiopathic pulmonary fibrosis. In one embodiment, the improved symptoms of the pulmonary disease may be measured by an increase of at least about 1, 2, 3, 4, 5, 7, or 10% or more of predicted forced vital capacity (FVC) relative to values measured in patients receiving treatment with a placebo over a period of at about six, twelve, eighteen months, or two or three years or more, preferably at least about a 12% or at least about 15% or even 20% increase in FVC. In another embodiment, the treatment results in a reduction in mortality among patients receiving treatment of at least 5%, 10%, 25%, 50% or more over a period of about two or three years or more. The interferon may be interferon α, interferon β or interferon γ.

In another embodiment, the subject suffering from the pulmonary disease, such as, for instance, IPF, chronic obstructive pulmonary disease (COPD) or asthma, is unresponsive to treatment with one or more of a corticosteroid, cyclophosphamide, and azathioprine. Furthermore, in patients that are minimally responsive to immunosuppressant therapies, wherein there is a modest, but insignificant improvement in pulmonary function tests, it is a further aspect of the invention to combine treatment of these patients with an aerosolized interferon while maintaining treatment with one or more other therapeutic regimens, including but not limited to treatment with one or more immunosuppressive or anti-inflammatory agents.

In more specific embodiments, aerosolized interferon is administered in doses ranging from 10 µg to 1000 µg, preferably about 50 µg to 750 µg or 75 µg to 500 µg or 100 µg to 250 µg, preferably given in a nebulizer from one to ten times per week, preferably about two, three, four or five times per week. In another embodiment, a dose of 100 µg to 500 µg is given in a nebulizer three times per week. Lower doses may be given depending on the efficiency of the nebulizer. When it is desired to treat patients with a combination of interferon-γ therapy and other treatment modalities, the aerosolized interferon-γ may be titrated to ensure no undesirable effects are experienced by these patients. Furthermore, when combination therapy is a consideration, the other agents may be delivered by a means in which they are considered to be the most effective. This may include intravenous, intramuscular, subcutaneous, or may be combined with INF-γ and delivered as an aerosol.

In still other specific embodiments aerosolized interferon is administered in doses and for time periods and by devices such as nebulizers sufficient to provide INF-γ that may be measured in the bronchoalveolar lavage fluid (BAL) of patients. The INF-γ may be present in the BAL fluid in amounts of at least 10, 25, 50, 100, 150, 200, 250, 300, 500 or even 750 or more picograms/milliliter. Further, in other specific embodiments aerosolized interferon is administered in doses and for time periods sufficient to produce a measurable decrease in the level of IL-8 present in the bronchoalveolar lavage (BAL) fluid of a patient of for instance, 10%, 20%, 30%, 40%, 50% or more. In some instances, the level of IL-8 in the BAL of a patient suffering from a pulmonary disease may be reduced to an amount that is no more than 100%, 50%, 25%, or 10% more than the level of IL-8 in the BAL fluid of a normal control substantially free of a pulmonary disease. In yet additional specific embodiments aerosolized interferon is administered in doses and for time periods sufficient to produce a measurable increase in the level of TGF-β present in the bronchoalveolar lavage (BAL) fluid of a patient of from 5%, 10%, 15%, 20%, 25%, or even 50%, 60%, 75% or 100% or more. The TGF-β may be measured in the BAL fluid after treatment in some instances in amounts of about 0.25, 0.50, 0.75, 1.00, 1.25, 1.50, 1.75, or 2.00 picograms/milliliter or more. In many instances, the aerosolized interferon is administered preferably in a nebulizer from one to ten times per week, preferably about two, three, four or five times per week. In each of these instances the interferon may be administered for time periods of one week, two weeks, five weeks, ten weeks, twenty weeks, thirty weeks, forty weeks, 50 weeks, sixty weeks, seventy weeks or more to attain the desired IL-8, TGF-β, or INF-γ levels.

In some embodiments, the nebulizer is chosen so as to provide delivery of at least about 10%, 15%, 20%, 25%, 30%, 35%, 40%, 50%, 60% or even 75% or more of the interferon present in the nebulizer to the lung, some provided to the middle lobe of the lung. It is desirable that no more than about 5%, 10%, 15%, 20%, 25%, 30%, 35%, 40%, or 50% of the interferon administered be deposited in the gastrointestinal tract, such as, for instance, in the stomach. Moreover, it is desirable that no more than about 5%, 10%, 15%, 20%, 25%, 50% or 75% of the interferon remain undelivered to a patient in a drug delivery container of a nebulizer. Still further, it is desirable that no more than about 5%, 10%, 15%, 25%, 30%, 35%, 40%, or 50% of the interferon remain in the oropharynx or mouth of a patient.

In another aspect, the invention features a method of accurately determining upper respiratory airway deposition of an agent administered by aerosol delivery. In one embodiment of this aspect of the invention, the agent administered via aerosol delivery is an interferon such as interferon α, interferon β or interferon-γ. This technology is unique and applies to the delivery of an interferon such as interferon α, interferon β or INF-γ to patients with all types of lung disease.

Other objects and advantages will become apparent from a review of the ensuing detailed description taken in conjunction with the following illustrative drawing.

BRIEF DESCRIPTION OF THE DRAWINGS

FIG. 5 depicts a deposition scan of a patient suffering with mixed connective tissue disease who has been treated three times per week for twelve weeks with 500 µg of INF-γ delivered via a nebulizer. Imaging was performed following a treatment. Regions of interest are shown as outlines. The deposition image is following inhalation of radiolabeled INF-γ aerosol; INF-γ deposited in lung=54 µg; sC/P=1.28, consistent with peripheral deposition. sC/P means the specific central to peripheral ratio described below. a/Xe means the aerosol to xenon ratio.

FIG. 10 demonstrates the amount of interferon-γ measured in the lungs of tuberculosis patients and patients with idiopathic pulmonary fibrosis both before and after aerosol treatment with interferon-γ.

FIG. 11 represents the percentage change in peak flow in asthma patients after treatment with aerosol INF-γ. All patients receiving aerosol interferon-γ were studied with spirometry to assess reversible airways disease. At each aerosol treatment, patients had monitoring of peak flows before and after treatment.

FIG. 13 provides the levels of interferon-γ measured in the BAL fluid of six patients both before and after treatment with aerosolized interferon-γ. Units are picograms of interferon-γ per ml of BAL fluid.

FIG. 14 depicts the levels of IL-8 measured in the BAL fluid of six patients both before and after treatment with aerosolized interferon-γ. Units are picograms of IL-8 per ml of BAL fluid.

FIG. 15 demonstrates the change in forced vital capacity (FVC) graphically among ten IPF patients treated with INF-γ compared to three control groups.

FIG. 16 demonstrates the change in FVC graphically among ten IPF patients treated with INF-γ compared to three control groups over a period of 30 weeks, nine IPF patients over a period of 40 weeks, and six IPF patients over a period of fifty weeks. One group of patients received no treatment at all (NYU Control Group), one group of patients received acetyl cysteine, one group of patients received etanercept, and two groups of patients received perfenadone. Three groups received placebo. These results demonstrate that patients suffering from IPF experience not only arrest of further deterioration but actual improved pulmonary function as demonstrated by increased FVC over time. To the contrary, patients receiving acetyl cysteine, etanercept, perfenadone or no treatment whatsoever demonstrate continued deterioration of pulmonary function as evidenced by decreased FVC over time.

FIG. 17 depicts the levels of IL-8 measured in the BAL fluid of six patients both before and after treatment with aerosolized interferon-γ and the levels of IL-8 measured in the BAL fluid of four normal patients. Units are picograms of IL-8 per ml of BAL fluid.

FIG. 18 depicts the levels of INF-γ measured in the BAL fluid of six patients both before and after treatment with aerosolized interferon-γ and the levels of INF-γ measured in the BAL fluid of four normal patients. The units are picograms of INF-γ per ml of BAL fluid.

DETAILED DESCRIPTION

Figure 1:
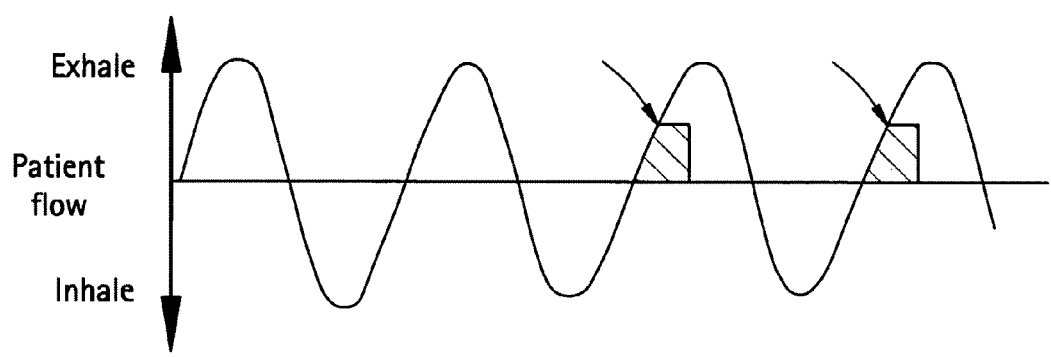
FIG. 1 describes a typical tidal breathing pattern.

Before the present methods and treatment methodology are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and described the methods and/or materials in connection with which the publications are cited.

Definitions

The term "improved symptoms," in a specific embodiment, is assessed as an improvement of at least 1% of predicted FVC relative to values prior to treatment.

The phrase "unresponsive to treatment with one or more of corticosteroid, cyclophosphamide, and azathioprine" means a patient population that is unresponsive to conventional prior art treatments.

Forced vital capacity (VC) means the total amount of air that can be moved in and out of the lungs.

Fev1 means the forced expiratory volume of air in one second.

Fev1/FVC ratio means the ratio of forced expiratory volume in one second and forced vital capacity.

The term "pulmonary disease" refers to any pathology affecting at least in part the lungs or respiratory system. The term is meant to encompass both obstructive and non-obstructive conditions such as, for instance, asthma, emphysema, chronic obstructive pulmonary disease, pneumonia, tuberculosis, mixed connective tissue disease and fibrosis in all its forms including but not limited to idiopathic pulmonary fibrosis.

The term "obstructive pulmonary disease" refers to any pulmonary disease that results in reduction of airflow in or out of the respiratory system. The reduction in airflow relative to normal may be measured in total or over a finite time, for example, by FVC or FEV1.

The term "idiopathic pulmonary fibrosis" (IPF), synonymous with "cryptogenic fibrosing alveolitis" (CFA) is the clinical term for a major subgroup of the idiopathic interstitial pneumonias, and it describes a disease characterized by idiopathic progressive interstitial disease with a mean survival from the onset of dyspnea of 3 to 6 years. A diagnosis of idiopathic pulmonary fibrosis is made by identifying usual interstitial pneumonia (UIP) on lung biopsy. The histological pattern is characterized by heterogeneity that includes patchy chronic inflammation (alveolitis), progressive injury (small aggregates of proliferating myofibroblasts and fibroblasts, termed fibroblastic foci) and fibrosis (dense collagen and honeycomb change).

The term "asthma" refers to a common disease that involves inflammation (cellular injury) and narrowing of the airways leading to the lungs. Asthma occurs in children and adults. Childhood asthma may continue into adolescence and adulthood, but some adults who develop asthma did not have asthma when they were younger. Millions of people worldwide are affected by asthma, which has become more common in recent years.

By "slow and deep breathing" is meant any breathing pattern wherein the time of inspiration is longer than the time of expiration. Such a pattern features a duty cycle (time of inspiration/total time of breath) of greater than 0.5. During normal tidal breathing the duty cycle is always less than or near 0.5. That is, the time of inspiration is always less than the time for expiration. In disease states, the duty cycle decreases in obstructive disease and for restrictive disorders it is likely to be still less than 0.5. "Slow and deep" breathing may feature an I/E ratio, time of inspiration relative to expiration of greater that 1, and in some instances the ratio may approach 8 or 9 thereby yielding a duty cycle of 0.8 or 0.9

Mechanisms of Action of Interferon-γ

Recombinant interferon-γ is commercially available as ACTIMMUNE® from InterMune, Brisbane, Calif. Signal transduction pathways have been recently studied in cultured cells delineating a temporal regulatory pathway for the response to INF-γ (Vilcek et al., (1994) *Int Arch Allergy Immunol* 104(4): 311-6; Young et al., (1995) *J Leukoc Biol* 58(4): 373-81). The first events take place when added INF-γ binds to the extracellular domain of its receptor, and leads to tyrosine phosphorylation of preexisting signal transducer and activator of transcription 1 (STAT-1) at the intracellular domain of the receptor. Only tyrosine-phosphorylated STAT-1 is activated, which allows it to form homodimers (or heterodimers) and bind to a specific DNA sequence.

Upon translocating to the nucleus and binding to its cognate regulatory element in the promoters of many genes, STAT-1 activates transcription. STAT-1 can work with other preexisting transcription factors that are constitutively active, and thus transcription of some genes is maximally induced without a need for new protein synthesis. Other genes are regulated by STAT-1 together with transcription factors that are newly synthesized in response to INF-γ. The IRF-1 gene, which also encodes a transcription factor, is also regulated by STAT-1 in response to INF-γ (Pine, R. (1992) *J Virol* 66(7): 4470-8; Pine et al., (1994) *Embo J* 13(1): 158-67; Pine et al., (1990) *Mol Cell Biol* 10(6): 2448-57). It should be noted that the promoter of the IRF-1 gene also contains binding sites for nuclear factor kappa B (NF-kB), which mediates tumor necrosis factor alpha (TNF-α)-activated transcription of the IRF-1 gene (Harada et al., (1994) *Mol Cell Biol* 14(2):1500-9; R. Pine, unpublished).

Once the IRF-1 protein has been synthesized, it activates transcription of a temporally downstream set of genes. IRF-1 has been shown to regulate the INF-γ-induced expression of key genes involved in antigen processing and presentation, including TAP-1, LMP-2, and HLA-A and HLA-B class I major histocompatibility antigens (Johnson et al., (1994) *Mol Cell Biol* 14(2): 1322-32; White et al., (1996) *Immunity* 5(4): 365-76).

IRF-1 is phosphorylated, and manipulating the extent of phosphorylation affects its DNA-binding activity (Pine et al., (1990) *Mol Cell Biol* 10(6): 2448-57; Nunokawa et al., (1994) *Biochem Biophys Res Commun* 200(2): 802-7). However, there is no clear evidence that phosphorylation of IRF-1 is regulated in vivo. STAT-1 activity is dependent on tyrosine phosphorylation and is affected by the extent of serine phosphorylation. However, the abundance of latent STAT-1 is also regulated. Cells treated overnight with INF-γ have increased levels of STAT-1 protein, though the tyrosine phosphorylation and DNA-binding activity are only slightly greater than in unstimulated cells (Pine et al., (1994) *Embo J* 13(1): 158-67).

The study of gene expression and its regulation can provide information on other aspects of the overall immunological state. Specifically, functional effects of cytokine changes can be confirmed by determination of specific DNA-binding activities. For example, in T cells IL-12 leads to activation of STAT-4, while IL-4 leads to activation of STAT-6, the occurrence of Th1 and Th2 responses or a shift from one to the other may be reflected in the profile of STAT DNA-binding activities detected at a particular time (Darnell (1996) *Recent Prog Horm Res* 51:391-403; Ivashkiv, L. B. (1995) *Immunity* 3(1): 1-4).

Aerosolized Interferon-γ Treatment of IPF

Recently, a small randomized trial of patients with IPF were treated with subcutaneous interferon-γ (INF-γ) (Ziesche et al. (1999) *N. Engl. J. Med.* 341:1264-1269). Analysis of transbronchial biopsy specimens obtained prior to and six months into therapy with INF-γ, demonstrated that abnormal pretreatment increases in the profibrotic cytokines transforming growth factor-β (TGF-β) and connective-tissue growth factor (CTGF) were significantly reduced after treatment with INF-γ (Ziesche et al. (1999) supra). Patients treated with prednisolone alone had no change in levels of TGF-β and CTGF.

Delivery of Interferons

Aerosol Delivery

In a broad aspect of the invention, a method of treating pulmonary diseases including asthma and idiopathic pulmonary fibrosis (IPF) in a subject suffering from the pulmonary disease, comprising administering an aerosolized interferon such as -γ in a therapeutically effective amount wherein the symptoms of the pulmonary disease are improved or ameliorated. The improved symptoms may be an increase of at least 10% of predicted FVC relative to values prior to treatment. In a preferred embodiment, aerosolized INF-γ may be used for treating subjects suffering from asthma or IPF wherein the subjects are unresponsive to treatment with one or more corticosteroid, cyclophosphamide, and azathioprine. Furthermore, the administration of an aerosolized interferon such as INF-γ is calculated and optimized in patients with pulmonary fibrosis. Such administration may result in improvement in pulmonary function tests in patients.

Interferons such as INF-γ may be administered by several different routes, including intravenous, intramuscular, subcutaneous, intranasally and via aerosol. However, when treating a pulmonary process alone, delivery of medication directly to the lung avoids exposure to other organ systems. Effective administration of 500 μg INF-γ via aerosol three times per week for two weeks has been shown by bronchoalveolar lavage (BAL) analysis in normal patients to result in increased levels of INF-γ post-administration. Likewise, about 500 micrograms of interferon-β three times per week and about 0.25 mg of interferon-α three times per week is thought to be effective.

It is an object of the present invention to deliver the interferon such as interferon-γ via the pulmonary route of administration. Interferons like INF-γ are delivered to the lungs of a mammal while inhaling and traverses across the lung epithelial lining to the blood stream. (Other reports of this include Adjei et al., PHARMACEUTICAL RESEARCH, VOL. 7, No. 6, pp. 565-569 (1990); Adjei et al., *International Journal of Pharmaceutics,* 63:135-144 (1990); Braquet et al., *Journal of Cardiovascular Pharmacology, Vol.* 13, suppl. 5, s. 143-146 (1989); Hubbard et al., *Annals of Internal Medicine*, Vol. III, No. 3, pp. 206-212(1989); Smith et al., *J. Clin. Invest.,* Vol. 84, pp. 1145-1146 (1989); Oswein et al., "*Aerosolization of Proteins*", Proceedings of Symposium on Respiratory Drug Delivery II, Keystone, Colo., March, 1990; and Platz et al., U.S. Pat. No. 5,284,656. Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the ULTRAVENT® nebulizer, manufactured by Mallinckrodt, Inc., St. Louis, Mo.; the ACORN II® nebulizer, manufactured by Marquest Medical Products, Englewood, Colo.; the VENTOLIN® metered dose inhaler, manufactured by Glaxo Inc., Research Triangle Park, N.C.; and the SPINHALER® powder inhaler, manufactured by Fisons Corp., Bedford, Mass., MISTYNEB ®, manufactured by Allegiance, McGraw Park, Ill.; AEROECLIPSE®, manufactured by Trudell Medical International, Canada, and the I-NEB® manufactured by Philips Respironics.

All such devices require the use of formulations suitable for the dispensing of protein. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified protein may also be prepared in different formulations depending on the type of chemical modification or the type of device employed.

Formulations suitable for use with a nebulizer, either jet or ultrasonic, may typically comprise protein dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device may generally comprise a finely divided powder containing the protein suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device may comprise a finely divided dry powder containing protein and may also include a bulking agent, such as lactose, sorbitol, sucrose, or mannitol in amounts which facilitate dispersal of the powder from the device, e.g., 50 to 90% by weight of the formulation. The protein should most advantageously be prepared in particulate form with an average particle size of less than 10 μm (or microns), most preferably 0.5 to 5 μm, for most effective delivery to the distal lung.

It is a goal of aerosol delivery to significantly increase the delivery of therapeutic agents such as interferons, including INF-γ, to the deep lung in humans. A particularly preferred approach to breathing slow and deep inspiration may, when compared with standard (tidal breathing), increase deposition efficiency in the lung periphery by a factor of up to about 50 times.

Figure 2:
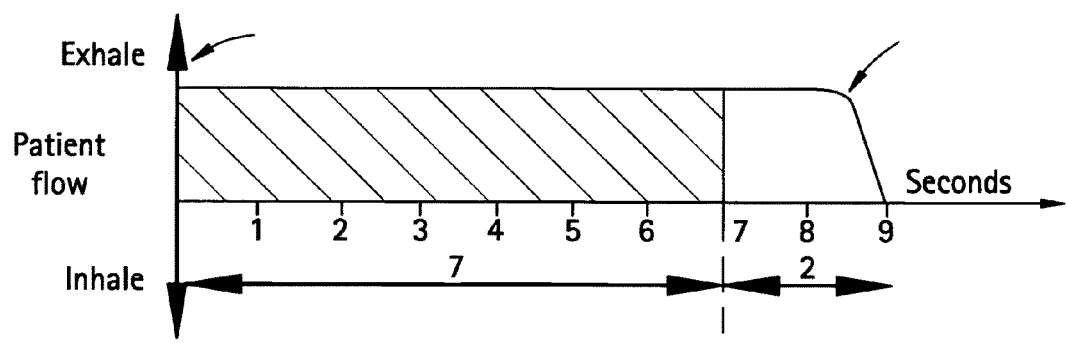
FIG. 2 describes a reduction in inspiratory flow and a greatly prolonged inspiratory time characteristic of a method of slow and deep inspiration as compared to tidal breathing.

The specific pattern of breathing using a method of slow and deep inspiration as compared to tidal breathing (FIG. 1) describes a reduction in inspiratory flow and a greatly prolonged inspiratory time. This pattern is shown in FIG. 2. The slow inspiration allows aerosol particles to bypass the upper airways thus making them available for deposition in the lung. The prolonged inspiration allows for suitable settling of aerosols in the lung periphery. The prolongation of the inspiratory time and the advanced settling promotes "inspiratory deposition" before remaining particles can be exhaled. It is possible under these circumstances to have almost 100% of the inhaled particles depositing before exhalation begins. This process can be further enhanced by using particles that are relatively large (e.g., about 4.5 μm) that ordinarily would deposit in the oropharynx. The prolonged inspiration of slow and deep breathing is particularly suited for delivery of drugs to the lungs of patients whose peripheral airway pathology results in reduced deposition of conventional smaller aerosols as well as promoting avoidance of deposition in the oropharynx. Diseases of the lung periphery that may be treated by this method include, for example, idiopathic pulmonary fibrosis and emphysema. Both these entities result in enlarged airspaces that result in minimal deposition during tidal breathing.

Figure 3:
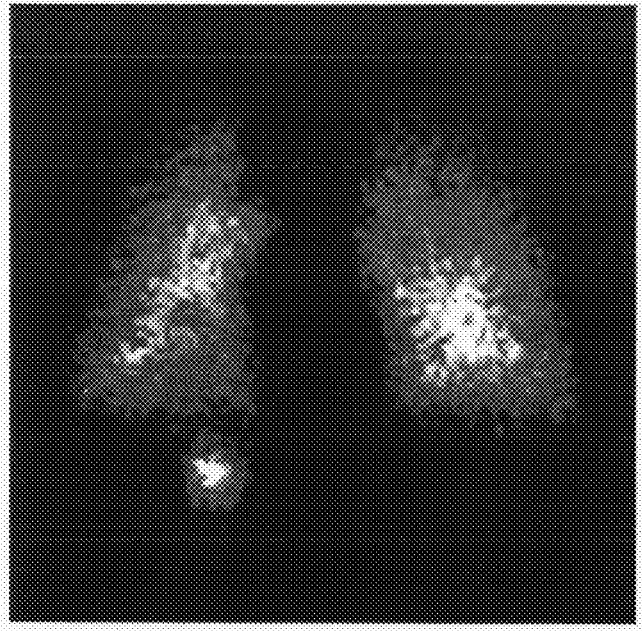
FIG. 3 represents a deposition pattern in a human subject inhaling 4.5 µm aerosols using the slow and deep breathing pattern. The images demonstrate minimal deposition of aerosol (less than 10%) in the upper airways illustrated by the small amount of activity in the stomach. The deposition image represents radiolabeled aerosol deposited in the lung periphery of a human subject after 3 breaths using the slow and deep pattern with an inspiratory time of approximately 8 seconds.
Figure 4:
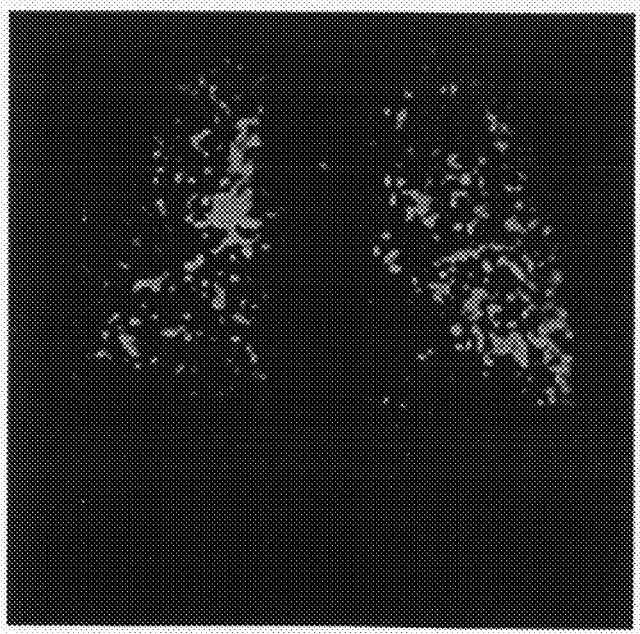
FIG. 4 is an illustrative scan in the same subject following 20 breaths of tidal breathing of 1.5 µm particles which is the present standard mode of inhalation. Analysis of the images indicates that the slow and deep method of breathing which incorporates the use of large particles, slow inspiration and a prolonged inspiratory time is 51 times more efficient per breath in depositing aerosol particles in the lung.
Figure 6:
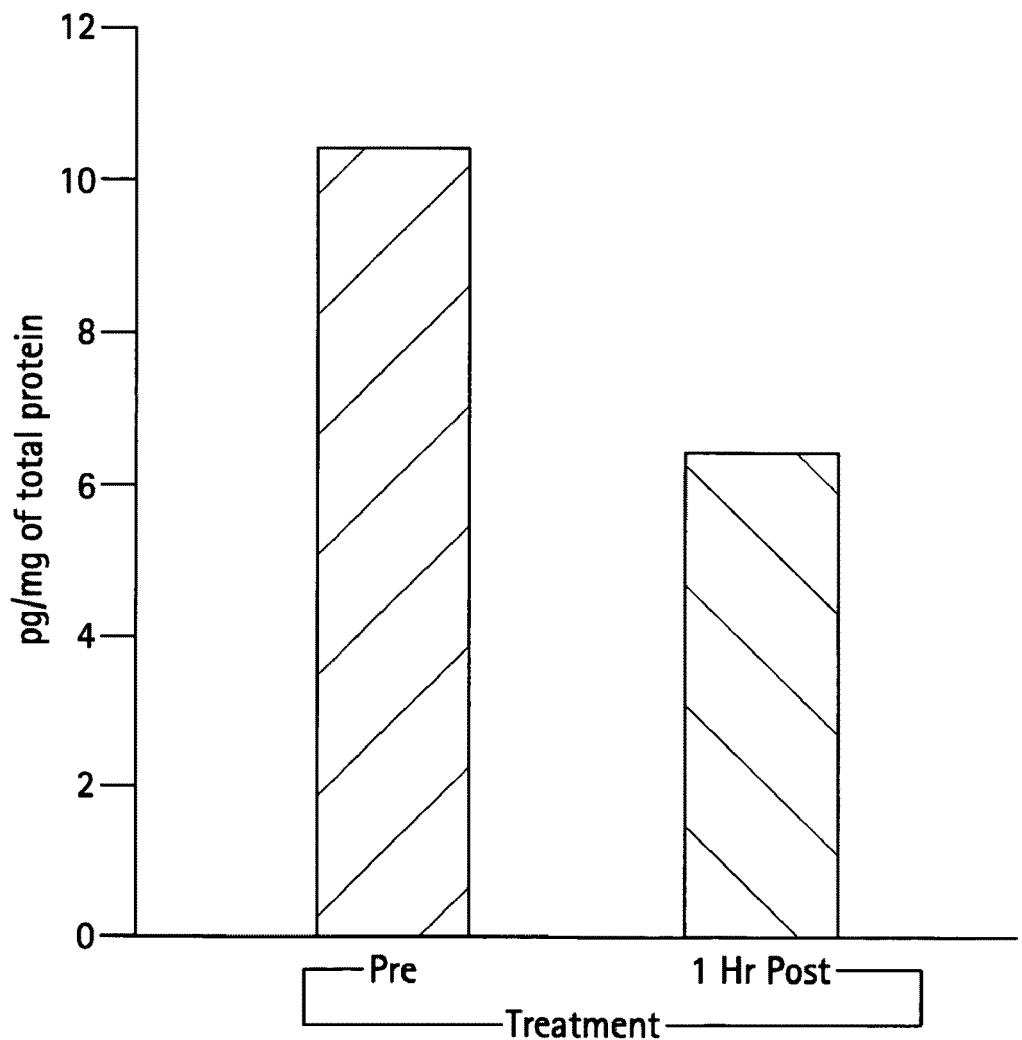
FIG. 6 represents TGF-β levels measured via BAL before and after aerosol therapy.

This technique of inhalation and deposition can enhance the peripheral delivery of drug with the intent of promoting systemic absorption into the systemic circulation via the pulmonary capillaries. FIG. 3 represents a deposition pattern in a human subject inhaling 4.5 μm aerosols using the slow and deep breathing pattern. The images demonstrate minimal deposition of aerosol (less than 10%) in the upper airways illustrated by the small amount of activity in the stomach. The deposition image represents radiolabeled aerosol deposited in the lung periphery of a human subject after 3 breaths using the slow and deep pattern with an inspiratory time of approximately 8 seconds. FIG. 4 is an illustrative scan in the same subject following 20 breaths of tidal breathing of 1.5 μm particles which is the present standard mode of inhalation. Analysis of the images indicates that the slow and deep method of breathing which incorporates the use of large particles, slow inspiration and a prolonged inspiratory time is 51 times more efficient per breath in depositing aerosol particles in the lung.

The manufacture of devices capable of performing the slow and deep maneuver is complex, but prototype devices that perform this function are being developed and have been utilized (Profile Therapeutics, Inc. 28 State Street, Ste. 1100, Boston, Mass. 02109, which is a subsidiary of Profile Therapeutics which has its main offices in the UK).

Diseases of the lung parenchyma result in geometric changes in the lung periphery that can minimize the deposition of inhaled particles. Therapeutics delivered directly to the site of disease (the lung periphery) can be more effective when compared to the same agent delivered systemically. A method of slow and deep inhalation of an , such as INF-γ, aerosol is particularly suited to the treatment of disease in the alveoli of patients with pulmonary fibrosis.

Human deposition studies have indicated that a slow and deep inhalation method is about 50 times more efficient than conventional systems of aerosol delivery. This breathing pattern allows the design of clinical trials to test the efficacy of aerosol therapy for pulmonary diseases such as obstructive pulmonary diseases, including, for example, idiopathic pulmonary fibrosis or asthma with agents such as interferons, including, for instance, INF-γ, over a wide range of dosing to the lung periphery utilizing existing formulations of this agent. Quantities deposited in the lung are controlled by the pattern of breathing because virtually no aerosol is exhaled.

Nasal Delivery

Nasal delivery of the protein is also contemplated. Nasal delivery allows the passage of the protein to the blood stream directly after administering the therapeutic product to the nose, without the necessity for deposition of the product in the lung. Formulations for nasal delivery include those with dextran or cyclodextran.

Dosages

It is understood that as further studies are conducted, information will emerge regarding appropriate dosage levels for treatment of various conditions in various patients, and one of ordinary skill in the art, considering the therapeutic context, age and general health of the recipient, will be able to determine proper dosing. Generally, for injection or infusion, interferon-γ dosage will be between 100 μg of biologically active protein (calculating the mass of the protein alone, without chemical modification) to 750 μg (based on the same) given three times per week. More preferably, the dosage may be about 500 μg given three times per week. Generally, for injection or infusion, interferon-α dosage is generally 250 to 750 micrograms administered one to five times per week, preferably about 500 micrograms administered three times per week. In the instance of interferon-β, dosage is generally 0.10 to 1 mg one to three times per week, preferably about 0.25 mg three times per week. The dosing schedule may vary, depending on the circulation half-life of the protein, and the formulation used.

Administration with Other Compounds

It is a further aspect of the present invention that one may administer the interferon in conjunction with one or more pharmaceutical compositions used for treating a pulmonary disease. Also, anti-inflammatory or immunosuppressive agents may be co-administered, eg. cyclophosphamide, azathioprine or corticosteroids. Administration may be simultaneous or may be in serriatim.

It has been shown that after subcutaneous administration of 250 μg INF-γ for three days, there was no increase in BAL levels of INF-γ or alteration of alveolar macrophages, while there was upregulation of peripheral blood monocytes (Jaffe et al. (1991) *J. Clin. Invest.* 88:297-302). In addition, aerosol INF-γ has been used as adjunctive therapy in patients with pulmonary tuberculosis.

In the studies described below, patients unresponsive to conventional immunosuppressive therapy suffering from IPF were treated with aerosolized INF-γ.

The invention may be better understood by reference to the following examples, which are intended to be exemplary of the invention and not limiting thereof.

EXAMPLES

The following examples are put forth so as to provide those of ordinary skill in the art with a complete disclosure and description of how to make and use the therapeutic methods of the invention and compounds and pharmaceutical compositions, and are not intended to limit the scope of what the inventors regard as their invention. Efforts have been made to ensure accuracy with respect to numbers used (e.g., amounts, temperature, etc.), but some experimental errors and deviations should be accounted for. Unless indicated otherwise, parts are parts by weight, molecular weight is average molecular weight, temperature is in degrees Centigrade, and pressure is at or near atmospheric.

Example 1

Patient Population

Study subjects were patients suffering from idiopathic pulmonary fibrosis (IPF) as diagnosed by the American Thoracic Society criteria A or B (below). The patient population had failed to respond to or was not a candidate for conventional therapy with corticosteroids, cyclophosphamide, and/or azathioprine. The patient population was treated with aerosolized INF-γ for twelve weeks.

In the setting of a surgical biopsy showing UIP, these three conditions must be met:

1. Exclusion of other known causes of interstitial lung disease, such as certain drug toxicities, environmental exposures, and connective tissue diseases.
2. Abnormal pulmonary function studies that include evidence of restriction (reduced vital capacity (VC) often with an increased Fev1/FVC ratio) and/or impaired gas exchange (increased alveolar-arterial gradient for $O_2$ or decreased diffusion capacity for CO).
3. Bibasilar reticular abnormalities with minimal ground glass opacities on HRCT scans.

In the absence of a surgical lung biopsy, in an immunocompetent adult, a presumed diagnosis of IPF may be made if:

I. All three above criteria are met.

II. A transbronchial lung biopsy (TBBx) or bonchoalveolar lavage (BAL) shows no features to support an alternative diagnosis.

III. Three of these four minor criteria:

1. Age>50
  2. Insidious onset of unexplained dyspnea on exertion
  3. Duration of illness>three months
  4. Bibasilar inspiratory crackles.

Improvement is defined as (1) An increase of 10% of predicted FVC from baseline value compared to FVC obtained prior to steroid therapy. (2) If a patient has a greater than 10% increase in FVC from baseline value and then returns to baseline value despite therapy.

Patients eligible for inclusion into the study are defined as follows:

Patients diagnosed with IPF based on accepted criteria (see above) within 3 years of screening;

Age 20-70;

A failed trial of prednisone with or without cyclophosphamide/azathioprine or patients in whom treatment with steroids or cytotoxic agents are contraindicated;

Patient taking 0-15 mg prednisone or the equivalent for 28 days prior to study enrollment and willing to remain on the same dose of corticosteroid;

FVC≧50% and ≦90% of predicted baseline value at screening;

$PaO_2$>60 mm Hg at rest on room air;

Patient able to understand and willing to sign a written informed consent and willing to comply with all requirements of the study protocol including Patient fits criteria for research bronchoscopy and is willing to undergo procedure;
Patient able to have medication administered three times per week at GCRC unit at Bellevue Hospital.

Patients ineligible for inclusion in the study are defined as follows: (1) Patient unwilling or unable to undergo research bronchoscopy; (2) Patient with known asthma or severe COPD; (3) Patient requiring oxygen therapy for maintenance of adequate arterial oxygenation; (4) Patient with hypersensitivity to study medication or other component medication; (5) Patient with known severe cardiac disease, severe peripheral vascular disease or seizure disorder which may be exacerbated by study drug administration (contraindications to drug administration as per package insert); (6) Pregnant or lactating females. Females of child-bearing age will be required to have negative pregnancy test and be required to use accepted form of birth control (abstinence for study duration is the preferred method); (7) Evidence of active infection within one week prior to treatment; (8) Any condition, other than IPF, which is likely to result in the death of the patient within one year from study enrollment; (9) Abnormal serum laboratory values including: (a) Liver function above specified limits: total bilirubin>1.5×upper limits of normal; alanine amino transferase>3×upper limit of normal; alkaline phosphatase>3×upper limit of normal; albumin<3.0 at screening; (b) CBC outside specified limits: WBC<2,500/mm3; hematocrit<30 or >59; platelets<100,000/mm3; (c) Creatinine>1.5×upper limits normal at screening; (10) Drugs for therapy for pulmonary fibrosis, excluding corticosteroids, cyclophosphamide, and/or azathioprine, within the previous six weeks; (11) Prior therapy with any class of interferon medication; (12) Investigational therapy for any indication within the last 28 days.

Example 2

Ten patients were recruited from the IPF registry to be enrolled in an open label pilot study of aerosolized interferon-γ. The ten patients fit the inclusion and exclusion criteria. Data collected included past medical history including height, weight, and vital signs; personal history of all medications and complete occupational and smoking history, physical exam, EKG, CBC, electrolyte panel, liver enzymes and coagulation profile, CXR, chest CT, PFT, ABG, an pregnancy test in females of child bearing age.

Each patient completed a Pulmonary Fibrosis Questionnaire at the beginning of the study which questioned extensively the tobacco exposure, environmental exposures, and medication usage throughout the patient lifetime. Each patient will complete a symptoms questionnaire which ascertains tolerability of INF-γ and possible side effects.

Baseline bronchoscopy with bronchoalveolar lavage (BAL) was performed to evaluate the levels of certain pro-fibrotic and inflammatory cytokines. The procedure was performed as follows:

Each patient was evaluated for bronchoscopy as per Bellevue Hospital Protocol. Each evaluation includes Hgb, platelets, BUN/CR, coagulation panel, ABG with PO2≧75 mm Hg, EKG, CXR. Contradictions to bronchoscopy include lack of patient cooperation, recent myocardial infarction, malignant arrhythmias, uncorrectable hypoxemia, unstable bronchial asthma, pulmonary hypertension, partial tracheal obstruction or vocal cord paralysis, bleeding diathesis, and uremia. The patients were NPO at least 8 hours prior to bronchoscopy. An intravenous line was placed, supplemental oxygen was administered, and continuous pulse oximetry and blood pressure monitoring were performed.

The patients were premedicated with 60 mg IM codeine, viscous lidocaine was applied to the nose and lidocaine gargle and nebulizer (topical anesthetic bronchoscope) were used. During the procedure, midazolam and/or morphine were sometimes administered to cause sedation and decrease the cough reflex. These medications are routinely used in bronchoscopy. The bronchoscope was passed through the nose and vocal cords, and an endobronchial exam was performed. BAL was then performed by administering 50 ml aliquots of sterile normal saline, for a total of 300 ml, and applying gentle suction for maximum return of fluid.

After BAL fluid was obtained from the patient; it was processed in the GCRC core laboratory under standardized protocol used for processing all BAL. BAL fluid was filtered through sterile gauze. A total cell count with differential was performed in a hemocytometer. Cell viability was determined by the Trypan Blue method. Twenty cytocentrifuge slides were prepared from each lobe of BAL fluid and frozen at −70° C. 24 hour supernatants were collected at a concentration of $10^6$ cells/ml for cytokine ELISA assays. The volume of epithelial lining fluid was determined according to the protein method. Following centrifugation, BAL fluid supernatant was concentrated 10×-50× using the AMICON filter method. Cytokine assays were carried out with commercially available kits (R&D Systems, Minneapolis, Minn.). All samples were assayed in triplicate, and the amount of cytokine was quantified at the end of the assay by a microtiter plater reader. Transbronchial biopsy specimens were processed for isolation of fibroblasts as previously described (Raghu et al. (1989) *Am. Rev. Resp. Dis.* 140:95-100) and analyzed for collagen production using $^3H$ proline incorporation into collagenous proteins. Each patient was monitored for potential side effects of bronchoscopy, including but not limited to fever, shortness of breath, hemoptysis, and pneumothorax for 4 hours post procedure in the GCRC by the clinical nursing staff. Concomitant medications were recorded in the patient's medical record.

Investigational therapies are not permitted while the patient is on the study. Pre-clinical rat studies have shown that parenteral INF-γ decreases the concentration of hepatic microsomal cytochrome P-450. This may cause a decreased metabolism of drugs known to utilize this degradation pathway. If a patient is on any medication known to be metabolized by this pathway, appropriate monitoring procedures are undertaken.

Patients were given a 100-μg/0.5ml vial of INF-γ given via I-Neb® (Philips Respironics) three times per week. Delivery to the lungs was assessed via radiolabeled gamma camera studies. One hour after medication delivery, a peak flow reading was obtained and recorded. After the first aerosol treatment, each patient was required to remain on the unit for an additional four hours, when an additional lung exam and peak flow measurement is taken. Each patient was monitored during the administration of INF-γ for side effects, including but not limited to fever, fatigue, GI abnormalities, headache, cough, shortness of breath, wheezing, and laboratory abnormalities.

Toxicity was graded with "The Common Toxicity Criteria". Dose modifications are made accordingly. For Grade I toxicity, the patient may continue treatment at the discretion of the physician. For Grade II toxicity (confirmed by immediately repeating abnormal laboratory parameters where appropriate) patient dose was held until a return to less than or equal to a Grade I toxicity, at which time the patient may resume treatment. If Grade II or worse toxicity returns, the patient was withdrawn from the study. For any Grade III or IV toxicity, the patient was withdrawn from the study.

Example 3

Clinical Efficacy

A 38 year old Haitian woman with history of chronic allergies presented with a one and half year history of progressively increasing shortness of breath and dyspnea on exertion. She was subsequently diagnosed as suffering from mixed connective tissue disease (MCTD). MCTD combines features of polymyositis, systemic lupus erythematosus, rheumatoid arthritis, scleroderma, and dermatomyositis, and is thus considered an overlap syndrome. MCTD commonly causes joint pain/swelling, malaise, Raynaud phenomenon, muscle inflammation, and sclerodactyly (thickening of the skin of the pads of the fingers). Distinguishing laboratory characteristics are a positive, speckled anti-nuclear antibody and an anti-U1-RNP antibody. It has been associated with HLA-DR4. The patient's PFTs showed a predominantly restrictive pattern with low diffusion capacity, suspicious for interstitial lung disease. She underwent a CT scan of her chest, which corroborated her PFT results, revealing subpleural fibrosis and honeycomb changes, predominantly at the lung bases. An open lung biopsy showed a pattern consistent with UIP/IPF.

Materials and Methods

The patient signed an informed consent approved by New York University School of Medicine Human Subjects Review Committee. Aerosol INF-γ (400 pg three times a week) was started in September of 2002 while the subject continued to receive 10 mg of prednisone daily. The nebulizer AERO-ECLIPSE® (Trudell International, Canada) was filled with 200 μg of INF-γ and normal saline solution to a final volume of 3 mL. The patient inhaled from the nebulizer using a relaxed pattern of tidal breathing until the device ran dry. It was refilled and the treatment repeated. The drug was administered at a flow rate of 8 L/min.

Pulmonary Function and Cardiopulmonary Exercise Testing

PFT and exercise testing were performed prior to starting INF-γ therapy and at the end of three months at New York University-Bellevue hospital. Subsequent PFT were performed at the discretion of the patient's private pulmonologist at the Hospital for Joint Diseases.

Shortness of Breath Assessment

The University of California, San Diego (UCSD) shortness of breath questionnaire (SOBQ) was completed by the subject prior to the start of and at the end of three months of therapy with INF-γ. Used extensively in pulmonary rehabilitation, the SOBQ is a self reported 24-item measure that assesses shortness of breath with various activities of daily living (ADLs). The patient indicated the severity of her shortness of breath on a six-point scale (0=not at all, to 5=maximal or unable to do due to breathlessness) as related to 21 different ADLs with varying degrees of exertion. If a particular activity was not preformed routinely, the patient was asked to estimate the anticipated degree of shortness of breath. The SOBQ was scored by summing responses across all 24 items to form a total score, which ranged from 0 to 122. Shortness of breath questionnaires have been shown to be a valid measure of health impairment in patients with chronic airflow limitation as well as restrictive lung diseases, and to respond to change with therapy.

BAL

The patient underwent a research BAL in one of the radiographically involved segments of the lung prior to the start of therapy and at the end of three months. A flexible bronchoscope was used for the BAL, with administration of xylocaine for local anesthesia. After six 50-mL aliquots of sterile saline solution were instilled, gentle suction was applied to allow recovery of bronchoalveolar fluid from a radiographically involved segment. The lavaged fluid was then filtered through two layers of gauze to remove mucus and centrifuged at 1,000 revolutions per minute for 10 min. The fluid was concentrated (3 to the 10×) [Centriprep-10; Amicon; Beverly, Mass.]. TGF-β was then measured by a purchased radioimmunoassay kit, in accordance with the manufacturer's recommendations (R & D; Minneapolis). A microtiter plate reader was used to determine concentrations. The sample was assayed in duplicate and the results are reported as picograms per milliliter of BAL fluid.

Deposition Study

The patient signed an informed consent as approved by State University of New York (SUNY) at Stony Brook, Committee on Research Involving Human Subjects. Details of the deposition technique were reported previously. (Condos et al., Chest 2004; 125: 2146-2155) Briefly, the patient was placed in a seated position in front of a gamma camera (Picker-Dyna 4C; Picker Corporation; Highland Heights. Ohio). For measurement of lung volume and ventilation, xenon 133 ($^{133}$Xe) gas was employed. $^{133}$Xe was introduced into a closed circuit of a "pulmonex"-Xenon trap (Atomic Products; Center Moriches, N.Y.) during tidal breathing after which a posterior equilibrium image was obtained. The patient then inhaled radiolabeled INF-γ aerosol. Two serial depositions were performed, each with a 200 μg dose of INF-γ. A background image was taken prior to the second nebulization. The patient swallowed a glass of water immediately after each nebulization, effectively washing any oropharyngeal activity into the stomach. In order to measure the attenuation correction (AC) for the chest wall, a calibrated injection of a known quantity of technetium 99m ($^{99m}$Tc)-macroaggregated albumin (5 to 10 mCi) was given through a peripheral intravenous line. Counts from a perfusion image taken after the injection were subtracted from a background image obtained prior to the injection. Net counts from the perfusion image were divided by the activity injected to yield an AC factor for the thorax (units=counts per min per microcurie). Analysis and storage of all images was obtained using image processing software (Nuclear Power 3.0.7; Scientific Imaging; Littleton, Colo.). The INF-γ aerosol particle distribution was measured using a protocol developed in the Stony Brook laboratory. Mass median aerodynamic diameter was 2.2 μm.

Regional Deposition

Regions of interest were drawn over the $^{133}$Xe equilibrium scan using computer software. Three separate regions were identified. The whole lung zone was labeled as the region encompassing both lungs, and the central zone was labeled as the region over the large central airways comprising 33% of the area of both lungs. The peripheral zone is the area which remains after deducting the central from the whole lung zone. These regions of interest overlying the $^{133}$Xe equilibrium image were then superimposed onto the $^{99m}$Tc deposition images. The ratio between central and peripheral (C/P) lung counts was calculated. In order to normalize this ratio for differences in relative lung thickness the C/P ratio for $^{99m}$Tc counts was divided by the C/P ratio for $^{133}$Xe counts. This ratio defines the specific C/P ratio. A specific ratio of 1.0 reflects deposition that is proportional to regional volume. A specific C/P ratio of unity reflects alveolar deposition as the central region outlines both central airways and the surrounding lung parenchyma. Increasing ratio in the C/P ratios greater than unity is consistent with increasing deposition in the proximal airways.

Results

Objective findings are listed in Tables 1 and 2. PFT performed at initial presentation revealed a predominantly restrictive pattern with reduced FVC (59% of predicted), TLC (53% of predicted), and DLCO/VA (51% of predicted). The patient was started on aerosolized interferon gamma in September of 2002 and had multiple PFT done showing interval improvement in her DLCO/VA (from 51% to 68%) and stabilization of her FEV1 and TLC. Her exercise performance revealed increased maximal oxygen consumption, decreased minute ventilation, and a reduction in the degree of oxygen desaturation. The patient had significant improvement in her SOBQ measurement (decrease by 19 points). BAL fluid assayed for TGF-β one hour after treatment with aerosol INF-γ was substantially reduced in comparison to pre drug treatment levels (FIG. 1). The first deposition image is shown in FIG. 2 (posterior scan). The AC value of the chest, measured by perfusion scan, was 184.4 counts per minute/μCi. Of the 400 μg INF-γ placed in the nebulizer (two 200 μg treatments), 54.4 μg or 13.6% was deposited in the lungs. Regions of interest are shown, derived from $^{133}$Xe equilibrium image and superimposed on the deposition image. The calculation of the specific C/P ratio, for deposition one and two, revealed ratios of 1.28 and 1.26 respectively. These ratios indicate a relative peripheral deposition (1.0 being the most peripheral possible).

The patient's chest CT showed no further progression in the bibasilar honeycomb changes or sub-pleural fibrosis for more than one year.

Discussion

Recent studies implicate repeated alveolar and epithelial injury and associated cytokine activation with resultant lung fibrosis. This case illustrates the potential use of aerosol INF-γ as a novel mode of therapy, bringing pharmacologic doses of the drug, far greater than that which could be delivered by subcutaneous injection, directly to the site of disease. At present levels of deposition in the lung parenchyma our patient demonstrated stabilization of her pulmonary function parameters. FVC and TLC<78% of predicted have been shown to have a negative impact on survival in patients with idiopathic interstitial pneumonias (Erbs et al., Chest 1997; 111: 51-57).

This patient had no significant decline in her FVC, and TLC over almost two years. She showed an improvement trend in her exercise physiology reaching 46% of her maximum oxygen consumption. A substantial decreased dyspnea score was noted at the end of 3 months as well as a significant decrease in the pro-fibrotic cytokine, TFG-β.

TABLE 1

PFT results before and after therapy

| | | % PREDICTED | | | |
|---|---|---|---|---|---|
| DATE | HISTORY | TLC | FEV1 | FVC | DLCO/VA |
| April-2002 | First PFT | 53 | 49 | 59 | 51 |
| July-2002 | After open lung Bx*; start of Tx† with prednisone and azathioprine | 51 | 57 | 55 | 64 |
| August-2002 | Azathioprine D/C due to ↑LFT; prednisone tapered to 10 mg/day; referred for research study; PRE Tx† PFT | 60 | 54 | 52 | 54 |

TABLE 1-continued

PFT results before and after therapy

| | | % PREDICTED | | | |
|---|---|---|---|---|---|
| DATE | HISTORY | TLC | FEV1 | FVC | DLCO/VA |
| December-2002 | Post INF-γ Tx† | 61 | 66 | 60 | 65 |
| June-2003 | Continued aerosol therapy BACK TO WORK | 54 | 67 | 61 | 61 |
| December-2003 | Continued aerosol therapy | 57 | 61 | 53 | 71 |
| July-2004 | Continued aerosol therapy | 53 | 58 | 51 | 68 |

*Bx = biopsy;
†Tx = treatment

TABLE 2

Results from exercise testing, dyspnea scores and muscle strength

| VARIABLE | Pre Tx† | Post Tx† (3 mo) |
|---|---|---|
| $V_E$ max L/min | 40.78 | 35.48 |
| $VO_2$ max, L/min | 0.655 (42%) | 0.746 (46%) |
| Minimum $O_2$ saturation (%) | 35 | 54 |
| UCSD SOBQ* | 63 | 44 |

*University of California at San Diego, Shortness of Breath Questionnaire
†Tx = treatment Example 4

BAL fluid is used for protein determination and assay of INF-γ using a viral inhibition assay to determine the amount of drug delivered. Concentrated BAL fluid and 24 hour cell culture supernatants are assayed for cytokines IL-1β, IL-4, IL-6, IL-8 and TNF-α by ELISA (R&D, Minneapolis). Cell-free BAL supernatant is used to measure TGF-β activity by ELISA and luciferase reporter assay. Transbronchial biopsy (TBBX) specimens are used to measure TGF-β gene transcription by semi-quantitative RT-PCR. Fibroblasts are obtained from TBBX specimens, and the quantities of collagen I, III, and fibronectin RNA measured by RT-PCR. RNA (10 μg) is obtained from TBBX or cell culture of TBBX, and Northern Blot analysis is performed. Hydroxyproline protein content is measured by spectrophotometry using BAL fluid, BAL supernatants, and TBBX specimens. BAL fluid cell counts are calculated for each patient, in both pre- and post-treatment samples. A blood sample from each patient is obtained for storage.

Example 5

Five usual interstitial pneumonia (UIP) or IPF patients were studied. Each patient was asked to participate in a deposition study (under separate consent) of INF-γ administered via hand-held nebulizer. This deposition study was designed to study aerosolized INF-γ as follows. The drug was labeled with 99mTc and administered via aerosol nebulizer. Using the "attenuation technique", the dose of INF-γ delivered to various regions of the lung was calculated. The initial dose of 500 μg INF-γ was used, as this dose has previously been shown to be safe. The dose is adjusted according to deposition studies in each individual patient. A follow up bronchoscopy was performed at the end of the therapy, using the protocol described above. BAL was guided by lung deposition images, so that the areas of highest drug deposition was analyzed and compared to areas of lowest delivered drug and pre-aerosol INF-γ samples. In this way, total dose to each area of the lung can be calculated and determined. Depending on clinical response and BAL data, dose may be adjusted to reflect optimal clinical and deposition parameters. Attempts will be made to sample similar segments pre- and post-treatment, when possible. Each patient has a follow up evaluation at one month post therapy. The results of all procedures, laboratory evaluations, radiological studies, and pulmonary physiology evaluations are documented in the patient's medical record. All study evaluations are conducted at the GCRC of NYU Medical Center.

One commercially available breath-actuated nebulizer was used in this study, the AeroEclipse, whose particle generation is dependent on patient breathing through the nebulizer. It produces aerosol only during inspiration.

INF-γ was radiolabeled using $^{99m}$Technetium diethylene triaminepenta-acetic acid ($^{99m}$Tc-DTPA) for both in vitro and in vivo studies. For AEROECLIPSE®, 2 vials (250 mg of INF-γ) were used to make up a final volume of 2 mL. Aero-Eclipse was operated using a Pari Master air compressor (PARI Respiratory Equipment, Inc. Monterey, Calif.)

The nebulizers were connected to the circuit in the manner of their clinical use. A ten stage, low flow (1.0 L/m) cascade impactor (California measurements, Sierra Madre, Calif.) was connected using a T connector (T connector$_{cascade}$, Hudson Respiratory Care, Temecula, Calif.). An inspiratory filter, that prevented particles from entering the cascade impactor during expiration, was placed between the piston pump and cascade impactor. A second filter (leak filter) was placed in the system to capture the excess particles directed neither to the inspiratory filter nor to the impactor. To assess possible effects of patient ventilation a piston pump (Harvard Apparatus, Millis, Mass.) was used to simulate a patient's breathing effort.

Prior to inhalation the aerosol was studied on the bench under two conditions:
Standing cloud: The cascade impactor sampled the particles directly from the tubing at 1 Lpm without any ventilation generated by the piston pump (pump disconnected from circuit). For the purpose of generation of particles from Aero-Eclipse, the breath actuation valve was pressed manually for the duration of sampling.

During Ventilation: The Harvard pump was used to generate a sinusoidal flow in the system, analogous to the breathing of a patient. A tidal volume of 750 mL; Respiratory Rate of 20/m and Duty Cycle of 0.5 was used.

Aerodynamic particle distributions were measured as well as deposition on the connecting tubing to the cascade (T connector$_{cascade}$). The ballistic properties of the aerosol were quantified as the activity on the T connector$_{cascade}$ and reported as a percentage of the activity captured in the cascade impactor (%Cascade). This deposition was used in predicting lung deposition.

Xenon imaging and attenuation studies For all the subjects INF-γ deposition was studied using the AEROECLIPSE® nebulizer. Xenon imaging and attenuation studies (see below) were performed.

Lung volume and outline studies ($^{133}$Xenon ($^{133}$Xe) equilibrium scan) The patient was seated in front of a posteriorly positioned gamma camera (Picker Dina camera; Northford, Conn.). After taking a room background image for $^{99m}$Technetium ($^{99}$m Tc), the camera was set for $^{133}$Xe. Breathing tidally at functional residual capacity (FRC), the patient inhaled 5-10 mCi of $^{133}$Xe until the count rate became stable±10% over 15 seconds. A 1.0 min gamma camera image ($^{133}$Xe equilibrium image) was acquired and stored in a computer (Nuclear Mac v1.2/94; Scientific Imaging Inc. Littleton, Colo.) for analysis. This image was used to define the outer margins of the lung.

Aerosol deposition studies After $^{133}$Xe imaging, the camera was switched to $^{99m}$Tc. Then, the patient inhaled radiolabeled aerosolized INF-γ from the nebulizer. For each device an expiratory filter was present to capture exhaled particles. The nebulizers were run until dry. After final inhalation, the patient drank a glass of water to wash material from the oropharynx to the stomach. Measuring stomach activity assessed upper airway deposition.

Lung attenuation studies (perfusion scan) Lung perfusion scanning was done to calculate the attenuation factor of the lungs. Immediately following deposition imaging, 5mCi of $^{99m}$Tc-albumin macroaggregates were injected via a peripheral vein. It was assumed that all the macroaggregates traversed the right side of the heart and distributed in the lung proportionately to regional perfusion. A one-minute image was obtained. Perfusion was calculated as measured activity minus the activity measured on the previous (deposition) image. The lung attenuation factor was measured by dividing the amount of activity measured by the camera by the amount of activity injected. Lung attenuation factor=Activity measured/activity injected Stomach Attenuation The patient was given bread with a known amount of $^{99m}$Tc applied to it and a gamma camera picture of the stomach was taken after ingestion. Stomach attenuation was calculated by dividing the activity ingested by activity measured by the gamma camera. Stomach attenuation factor =Activity measured/activity ingested Quantification of deposition Using the computer, regions of interest were visually drawn around the stored equilibrium $^{133}$Xe equilibrium scan to define the lung outline and encompass the lung volume. Central lung regions were then drawn that outlined the inner one third of the two-dimensional lung area. After the xenon regions were defined, the same regions were placed over the deposition image and stomach activity identified. Then, a "stomach region" was visually drawn outlining the stomach. If there was overlap between the stomach region and the xenon equilibrium region of the left lung, the overlapping region was defined as "stomach on lung" or SOL. For determination of whole lung deposition, radioactivity from the stomach and the stomach on lung regions were excluded.

Lung deposition was measured using the gamma camera by quantifying activity in the lung regions and applying the appropriate attenuation correction. Oropharyngeal deposition was determined by subtracting the lung activity from the total activity on the deposition image. Appropriate corrections were made for stomach attenuation.

Specific Central to Peripheral ratio (sC/P) Specific central to peripheral lung activity was defined by dividing the aerosol image by the xenon equilibrium image. This ratio represents the distribution of deposited aerosol normalized for regional lung volume. sC/P for aerosol deposition=(C/P aerosol/C/P xenon). If the aerosol behaves perfectly as a gas and follows the $^{133}$Xe distribution, the sC/P ratio should be 1.0. Particles that deposit preferentially in central airways yield sC/P ratios of 2.0 or higher.

Results of Deposition study show significant deposition of aerosol throughout the lungs. When normalized for lung volume, there are relatively more particles in central lung regions than peripheral (sC/P ratio=1.618. There is minimal upper airway deposition.

Example 6

Effects of aerosol INF-γ

Adverse effects We treated 15 individuals (normal volunteers and patients with pulmonary tuberculosis) with aerosolized INF-γ. The aerosol administration was well tolerated with few patients complaining of occasional cough or myalgias. The longest period of administration was 3 months without an increase in adverse effects. In addition, Jaffe found that aerosolized INF-γ given to normal subjects was safe, without systemic side effects, and was able to activate alveolar macrophages and not PBMC, as opposed to parenterally delivered r INF-γ, the effects of which could only be noted in the peripheral blood (Jaffe et al., (1991) *J Clin Invest* 88(1): 297-302).

Deposition studies We investigated the aerosol deposition characteristics of INF-γ. A deposition image reveals that radioactivity (aerosol) is deposited to all normal areas of the lung. Disease and cavitary areas are spared. Perfusion scan shows minimal perfusion to cavitary areas as well. Preliminary determination of deposition reveals a range of 10-20% of aerosol dose delivered to the lung, using both mass-balance technique and xenon (figure). We concluded that targeted delivery of drug to the lung results in drug deposition in normal lung parenchyma (Condos et al., (1998) *Am J Respir Crit Care Med* 157(3): A187).

Bronchoalveolar lavage findings. We previously demonstrated clinical improvement in a group of patients with severe multi-drug resistant tuberculosis treated with INF-γ. The patients underwent bronchoscopy with BAL of the radiographically involved area before and after treatment. 24-hour cell culture supernatants and fluid from the BAL were assayed by ELISA and were found to have decreasing levels over time of TNF-α (mean172 to 117 pg/ml), IL1-b (mean 25 to 8 pg/ml) and no appreciable levels of INF-γ (mean 3.3 to 2.5 pg/ml). We concluded that INF-γ administration is associated with a decrease in TNF-α produced locally at sites of disease. This may in part explain the beneficial effects of INF-γ in advanced in advanced MDR-TB (Condos et al., (1998) *Am J Respir Crit Care Med* 157(3): A187).

Example 7

Successful Treatment of Idiopathic Pulmonary Fibrosis

Figure 7:
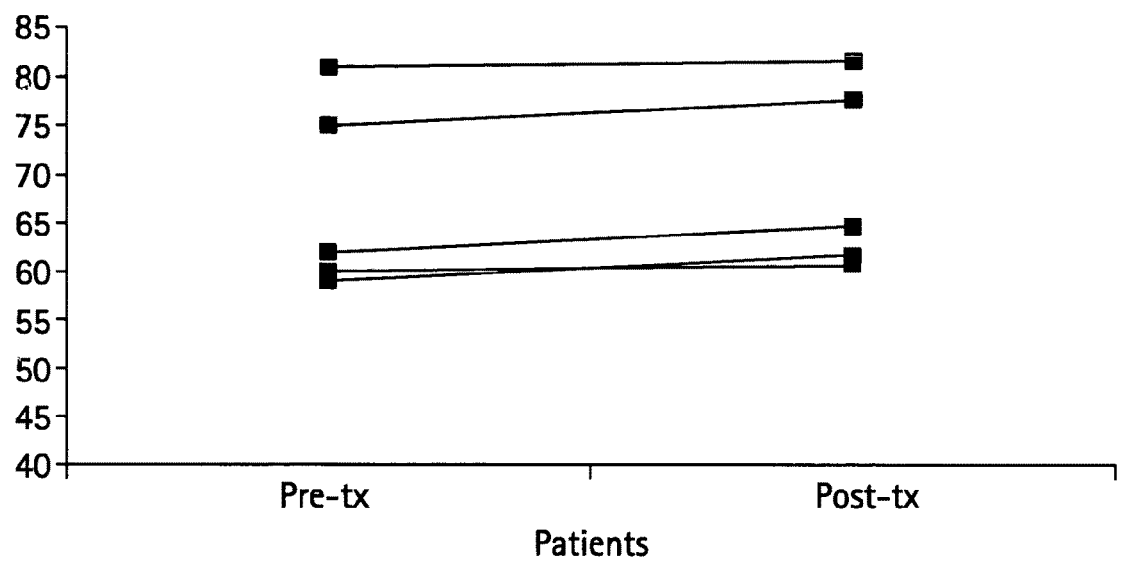
FIG. 7 demonstrates the increased percent predicted total lung capacity after treatment for five patients with IPF. All patients reported subjective improvements in their shortness of breath. By the end of three months of treatment, patients in the study had a statistically significant increase in total lung capacity.
Figure 8:
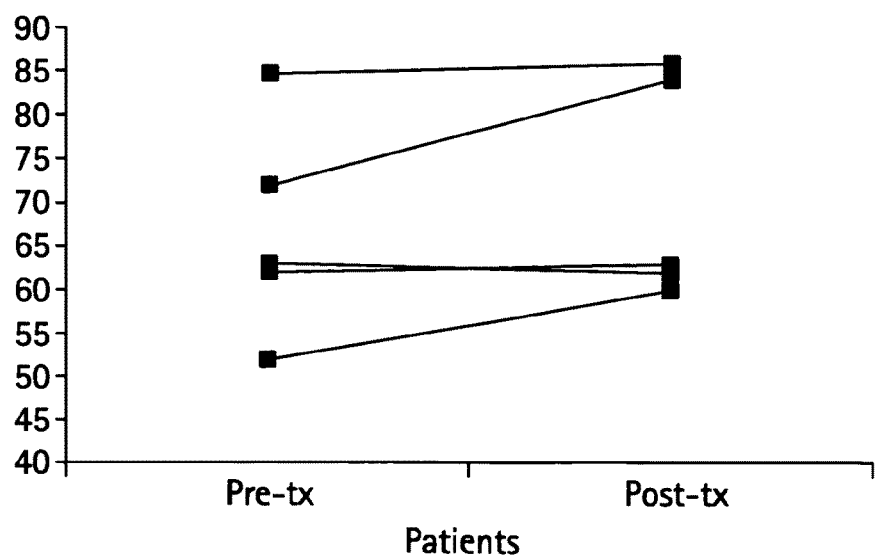
FIG. 8 demonstrates the increased percent predicted forced vital capacity after treatment in three of the five patients treated in a study of aerosol rINF-γ for five patients with IPF.
Figure 9A:
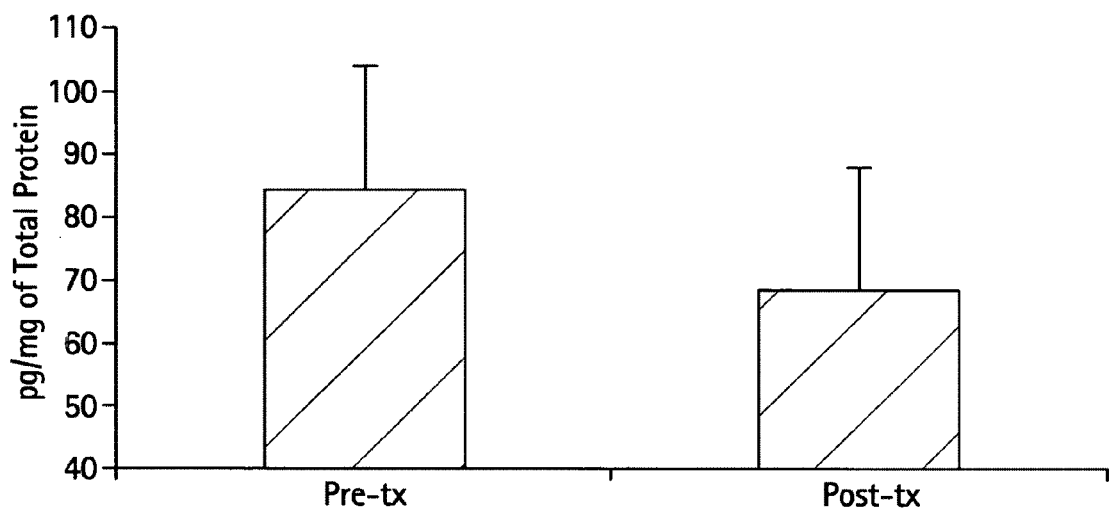
FIGS. 9A and 9B demonstrate the reduction of TGF-β (per mg total protein) in the five patients treated with aerosol rINF-γ for IPF. TGF-β is one of the key mediators of fibrosis in the lung. Its activation leads to collagen production. Decreases in its levels should lead to less collagen deposition and less fibrosis in the lung.
Figure 9B:
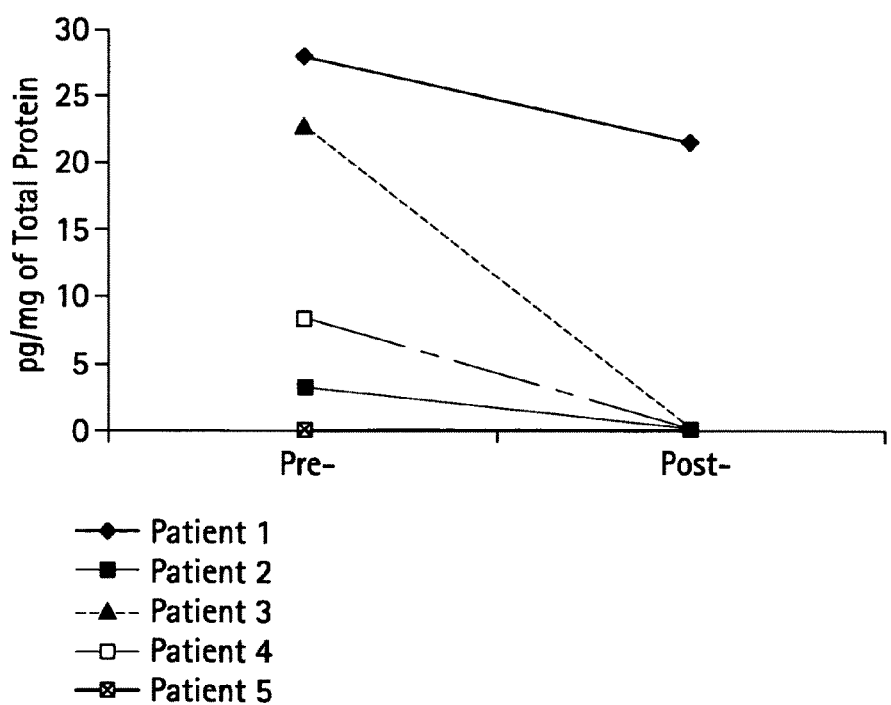

In a study of aerosol rINF-γ for five patients with usual interstitial pneumonia (UIP) or IPF, we found the treatment to be well tolerated. Adverse effects included fatigue, cough, and low grade fever (n=1). Routine laboratory assessment during the study period did not reveal any abnormalities. All patients reported subjective improvements in their shortness of breath. By the end of three months of treatment, patients in the study had a statistically significant increase in total lung capacity. FIG. 7 demonstrates the increased percent predicted total lung capacity after treatment in three of the five patients treated. There was also an improvement of greater than 200 cc's (200 and 500 cc, respectively) in the Forced Vital Capacity in two of the five study patients. FIG. 8 demonstrates the increased percent predicted forced vital capacity after treatment in three of the five patients treated. These physiologic changes were accompanied by decreases in the levels of activated TGF-β recovered from broncheoalveolar lavage (BAL) fluid (fluid washed from the inside lining of the lungs) of these patients. FIG. 9 demonstrates the reduced portion of TGF-β of total protein in the five patients treated. TGF-β is one of the key mediators of fibrosis in the lung. Its activation leads to collagen production. Decreases in its levels should lead to less collagen deposition and less fibrosis in the lung. In addition, we measured levels of -γ in the BAL fluid of the patients before and after aerosol therapy and found an increase associated with aerosol administration of the drug. FIG. 10 demonstrates the amount of interferon-γ measured in the lungs of tuberculosis patients and patients with idiopathic pulmonary fibrosis both before and after aerosol treatment with interferon-γ.

In contrast to subcutaneous studies previously performed, we were able to show that there was a physiologic improvement in lung function with aerosol delivery of rINF-γ. This improvement occurred over a treatment period of three months compared to the one year treatment received by the patients in another subcutaneous trial. This physiologic improvement was associated with increases in levels of INF-γ in the lung leading to decreases in levels of activated TGF-β recovered from the lungs of patients after aerosol treatment. This data demonstrates the ability to deliver a pharmacologically important amount of interferon-γ to the lung. No detectable lung levels of interferon-γ were measured following subcutaneous administration. (See, Jaffe et al., *J Clin Invest.* 88, 297-302 (1991). In an effort to further define lung dose, two of the five patients had deposition studies performed. These studies confirmed deposition of approximately 40 mcg of rINF-γ to the lung periphery. No measurements of lung dose or lung levels of rINF-γ were measured or reported the subcutaneous rINF-γ trial.

Example 8

Cytokine Gene Regulation

In this study investigation of transcription factor abundance, phosphorylation, and DNA binding activities test the hypothesis that aerosol INF-γ treatments impinge on cellular signal transduction pathways to activate latent STAT-1 and induce de novo synthesis of IRF-1. We performed these experiments on BAL cells obtained from uninvolved and involved areas of lung in patients with pulmonary TB pre and post treatment with INF-γ (Condos et al., (1999) *Am J Respir Crit Care Med* (in press)). Purifying and cloning IRF-1 was a principal part of the initial work performed by Richard Pine, Ph.D., in the Laboratory of Molecular Cell Biology at Rockefeller University with James E. Darnell, Jr. (Pine et al., (1990) *Mol Cell Biol* 10(6): 2448-57). Immunoblot and electrophoretic mobility shift assays the same as or similar to those proposed for Aim 3 of this project have been employed in the work mentioned here.

The results of cytokine gene manipulation in the uninvolved lungs of tuberculosis patients are most relevant. Results show that in both the adherent (mainly alveolar macrophages) and the nonadherent (lymphocytes and polymorphonuclear cells) portions of the BAL cells, there is an increase in the amount of specific IRF-DNA and STAT-1-DNA complexes after aerosol INF-γ treatment.

Example 9

Efficacy in Asthma Treatment

We will recruit 30 patients with mild to moderate asthma to receive INF-γ aerosol versus standard treatment. The study will be performed as a randomized, placebo controlled, crossover, double-blind r INF-γ aerosol delivery study in subjects with mild-moderate persistent asthma requiring moderate dose inhaled corticosteroid for symptom control.

Patients must be between the ages of 18 and 65 yr., any race or sex. They must be current nonsmokers with <10 pack year history of cigarette smoking. Patients who meet NAEPP guidelines for a diagnosis of asthma will be enrolled. We will recruit patients with mild-moderate persistent asthma, with baseline forced expiratory volume in one second (FEV1) greater that 70% of predicted value and evidence of reversibility (≧15% improvement in FEV1 post-bronchodilator treatment). These patients will be required to be on intermittent use of inhaled B2-agonists and low dose inhaled corticosteroids. Low dose inhaled corticosteriod use includes 168-500 mcg/day of beclomethasone dipropionate, 200-400 mcg/day of budesonide DPI, 500-1000 mcg of flunisolide, or 400-1000 mcg/day of triamcinolone acetonide.

Patients who are pregnant, have contraindications to fiber optic bronchoscopy, are current smokers, or have a >10 pack year history of cigarette smoking will be excluded. Any patient with a history of poorly controlled or severe asthma, history of recent systemic corticosteroid use, or history of recent exacerbation or infection will also be excluded.

We will incur a 1 month "wash-in" period to allow all recruited patients to start at the same baseline dosages of inhaled corticodsteroids (beclomethasone dipropionate 4-12 puffs/day). Each patient will have at baseline:
1) Complete history and physical examination and routine laboratory work,
2) Pulmonary function measurements (FEV1, FVC, and PEFR),
3) 50 ml heparinized blood drawn by venous stick,
4) Blood samples will be obtained for total IgE, specific IgE to defined allergens, and eosinophil count,
5) Fiberoptic bronchoscopy with BAL, with analysis of cell count/differential and levels of INF-γ, IL-4, IL-5, GM-CSF, IL-10, IL-12, and IL-13 by ELISA of 24 hour culture supernatants.

We will then administer aerosol r INF-γ (500mcg) 3 times a week for 8 weeks to 15 patients. Equivalent amounts of aerosolized saline will be administered to 15 patients in a randomized fashion. At eight weeks we will allow for a 1 month wash out period and cross over the subjects to the second arm of the trial.

The patients will have at each treatment visit:
1) Brief questionnaire regarding signs and symptoms.
2) Review of daily diary cards and monitor use of b-agonists.
3) Peak flow monitoring before and after aerosol treatment
4) Abbreviated history and physical exam performed weekly.
5) Subjects will characterize symptoms in a daily diary before, during, and after aerosolized INF-γ treatment. They will rate symptoms of cough, wheeze, and shortness of breath on a scale. They will also record daily peak flow measurements.

At completion of each arm of the trial (at eight weeks of either aerosolized INF-γ treatment or control saline) subjects will have:
1) Complete history and physical examination and routine laboratory work.
2) Pulmonary function measurements (FEV1, FVC, and PEFR)
3) 50 ml heparinized blood drawn by venous stick.
4) Blood samples will be obtained for total IgE, specific IgE to defined allergens (RAST), and eosinophil count.
5) Fiberoptic bronchoscopy with BAL will be performed the day after the last INF-γ treatment or no treatment. We will analyze BAL cell count/differential and levels of INF-γ, IL-4, IL-5, GM-CSF, IL-10, IL-12, and IL-13 by ELISA of 24-hour culture supernatants.
6) All patients will continue to be followed monthly in the asthma clinic:
a) complete history and physical
b) routine labs
c) spirometry and peak flow measurements We have chosen to study patients with mild-moderate persistent asthma on low dose inhaled steroids for a variety of reasons. First, to include only patients with mild intermittent symptoms may not allow us the sensitivity of finding physiologic, symptomatic, or immunologic changes in such a population. Second, we cannot allow any of our patients requiring inhaled steroids to discontinue treatment for this trial. In addition, the purpose of this trial is to determine if aerosolized INF-γ can serve as an adjunct to already specified treatment regimens. We understand that the use of inhaled steroids may confound our study as corticosteroids can affect cytokine levels. We will include a "wash in" period to start all subjects at the same baseline.

Example 10

Effect on Pulmonary Function of Asthmatics

To determine the effects of aerosol r INF-γ on pulmonary function measurements, we will obtain spirometry values of forced expiratory volume at one second (FEV1), forced vital capacity (FVC), peak expiratory flow rate, and lung volumes including total lung capacity (TLC), and functional residual capacity (FRC) for each subject prior to aerosolized treatment. These will be performed in the Bellevue Hospital Pulmonary Function Laboratory.

We expect to find a mild improvement in peak flow measurements immediately following administration of aerosolized r INF-γ, as we have noted in treating tuberculosis patients who did not have asthma. Currently, it is unclear why INF-γ would have a bronchodilator effect. We also expect an improvement in FEV1, and FVC after 8 weeks of aerosol INF-γ treatment, reflecting reduced airway inflammation.

We choose to follow FEV1 particularly because it is reproducible for individual patients. These values are specific for large airway obstruction. Should we find during the initial portion of the study that other variables of small airways disease is affected, we will use specific airways conductance, airways resistance, or forced expiratory values at 25-50% as endpoints. Should more sensitive tests of airway resistance be required, we may perform frequency dependence of compliance studies. We can also perform bronchial provocation studies with methacholine to study airway hyperreactivity. These additional studies are not as reliable because of individual variability as well as interindividual variability. The study design as a cross-over trial should avoid interindividual variability.

Example 11

Effects on BAL specimens

BAL specimens will be obtained from the 30 asthma patients. We will administer aerosol INF-γ to 15 of these patients for 8 weeks in order to assess whether INF-γ modulates cytokine production. These patients will have pre- and post-treatment BAL and blood draws.

Methods Fiberoptic bronchoscopy Subjects will be pre-screened with medical history and physical examination, spirometry, oximetry, assessment of bronchial hyperresponsiveness, coagulation tests (PT, PTT, platelets), and CBC and screening chemistries. During the procedure patients with have continuous monitoring of heart rate and O2 saturation, recording of subject symptoms and medication doses, intravenous catheter in place, premedication with inhaled b-agonist, subcutaneous atropine (0.4 mg), and sedation (midazolam, iv), and supplemental oxygen. The fiberoptic bronchoscope is introduced after light premedication and topical anesthesia of the nose and upper airway. The tip of the bronchoscope is wedged into a segmental, or subsegmental, bronchus of the right middle lobe or lingula. One hundred milliliters of 37° C. normal saline are instilled into the bronchus in aliquots of 20 ml. The warmed saline should avoid thermally induced bronchospasm in asthma subjects. Gentle intermittent suction is used to recover the effluent. Fluid recovery of 60 to 80% is expected in mild asthmatics. Recovery is reduced to 50% in subjects with moderate to severe disease [Jarjour, 1998 #62]. Pulse oximetry and clinical assessment of patient status will continue post-procedure. Discharge instructions will include follow-up appointment within the week, and contact telephone number.

Alveolar macrophages (AM) and BAL cells Cells will be collected by bronchoalveolar lavage (BAL) performed by standard techniques, and prepared for culture as follows: The fluid is filtered through one layer of sterile gauze to remove clumps of mucus. A total cell count is done in a hemocytometer and cell differentials performed on cytocentrifuge slides stained with modified Wright-Giemsa stain with a total of 500 cells counted. Cell viability is determined by Trypan Blue exclusion, and in all cases recovered cells to be used for experiments will be greater than 90% viable. Twenty cytocentrifuge slides will be prepared from each lobe of BAL and once fixed in 10% formalin, frozen at −70° C. BAL cells will be washed and cultured (37° C.) in RPMI (GIBCO) supplemented with 10% heat-inactivated fetal calf serum (FCS) and 100 u/mL penicillin and 100 mcg/ml streptomycin at a concentration of $10^6$ cells/ml for 24 hours.

Peripheral blood Blood will be obtained by venous stick at a constant time in the day, before and after completion of INF-γ treatment. PBMCs will be isolated from heparinized venous blood by Ficoll-Hypaque density gradient centrifugation. Heparinized venous blood is layered on Ficoll-Hypaque and centrifuged at 2500 rpm for 20 minutes. The low density layer of PBMCs will be aspirated and washed with phosphate buffered saline (PBS) and resuspended at a concentration of $10^6$ cells/ml of RPMI-1640 (GIBCO) with 10% heat-inactivated FCS, 100 U/ml penicillin, and 100 mcg/ml streptomycin. The cell cultures will then be incubated at 37° C. and 5% $CO_2$ for 24 hours. The cell supernatants will then be collected and assayed for cytokines by ELISA.

Serum samples will also be collected to determine specific IgE (RAST) to allergens associated with urban asthma (D. pteronyssinus, D. farinea, B. germanica —German cockroach, and P. americana—American cockroach).

An additional study will be performed on PBMCs obtained from atopic asthmatics and normal controls. This will entail PBM cell culture after isolation as described above in the same supplemented RPMI culture media. These cultured cells will then be stimulated with a nonspecific stimulus (LPS) or with a known allergen. The culture supernatants will then be assayed for cytokines by ELISA. These levels will be compared to resting cell cytokine levels. This evaluation can be done to screen a large urban population of asthma subjects for recruitment of patients with a baseline poor INF-γ response into the aerosolized INF-γ treatment trial.

Assessment of cytokines We will assay BAL cell supernatants collected over 24 hours at $10^6$ cells/ml by ELISA (Endogen) for INF-γ, IL-4, IL-5, IL-10, IL-12, IL-13 and GM-CSF. We collect 5 tubes of $10^6$ cells/ml so that we can run samples in triplicate for each cytokine. Since we average 30 to $40 \times 10^6$ BAL cells per lung segment, we can expect to evaluate BAL cell supernatants for each patient. We will not measure cytokines in BAL fluid, since we may retrieve INF-γ in the post-BAL specimens, and our interest is the release of cytokines from BAL cells spontaneously.

Example 12

Mechanisms of Gene Regulation Affected by INF-γ Treatment

The clinical treatment protocol will have clear-cut effects on the abundance and activity of transcription factors that regulate gene expression in response to INF-γ and that correlation of these data with the cytokine profile will extend the criteria by which the immune response in asthma can be evaluated. Furthermore, the data obtained will allow mechanistic interpretation of the results from analysis of cytokine production and expression of cytokine and other genes.

The design of the project incorporates several controls to help establish the effect of the aerosol INF-γ treatment, distinct from any other variable. These include obtaining BAL and blood samples before and after the course of treatment, and collection of BAL samples from uninvolved as well as involved lobes. All experiments for this aim will be done with protein extracts prepared from BAL or PBM cells. Cytoplasmic and nuclear proteins will be obtained and analyzed separately. To gain more definitive results, BAL cells will be separated into adherent and nonadherent populations. The former will include predominantly alveolar macrophages. The latter will be comprised predominantly of lymphocytes and granulocytes. PBMC will be extracted without further separation.

Investigation of transcription factor abundance and DNA-binding activities for this project will test the hypothesis that the clinical protocol of aerosol INF-γ treatments will impinge on cellular signal transduction pathways to activate latent STAT-1 and induce de novo synthesis of IRF-1 and CIITA. The data obtained will relate the molecular mechanisms that regulate gene expression to initial clinical observations. The results from a limited course of therapeutic in vivo treatment with aerosol INF-γ will have far greater predictive power for design of future trials when interpreted in conjunction with the data that demonstrate the molecular response to the therapy.

Determine abundance of transcription factors STAT-1, IRF-1 and CIITA There are two major reasons why it will be valuable to quantify the total amount of these transcription factors before and after the treatment protocol. These data will be critical for overall interpretation of the regulated response to the INF-γ treatments. It will lead to conclusions about the extent to which the available protein is subject to phosphorylation events and the proportion of total protein that has DNA-binding activity. Additionally, the abundance of the proteins is the final measure of regulated expression of the genes that encode the factors and thus provides a foundation for future studies to further integrate the functional and regulatory aspects of the evoked immune response. immunoblot detection will be the primary technique used. Cytoplasmic or nuclear extract from up to $5 \times 10^6$ cells will be used for each analysis. Obtaining cells as described above will yield 10 samples for each patient. All the extracts of PBMC and BAL cells from one patient will be included in a single experiment, which will facilitate relative quantitation within a set of samples. Control cytoplasmic and nuclear extracts prepared from cultured cell lines will also be included in each experiment. On the basis of previous studies, these samples will be known to contain the target proteins, and can thus provide positive controls for the immunoblot detection. Additionally, they can be used to validate that the data obtained are quantitative or reveal the limits of the quantitative detection.

The proteins will be separated by SDS-PAGE, then transferred to a membrane. The membrane will be developed with reagents to detect STAT-1, IRF-1, and CIITA, one after the other. The membrane will be probed finally to detect b-tubulin, which will be present in both cytoplasmic and nuclear protein extracts and can thus serve as an internal standard for quantitative comparison of cytoplasmic or nuclear extracts within and between experiments. All the antibodies needed are available in the laboratory or can be commercially obtained and are known to work for immunoblot protocols. To allow the sequential detection of different proteins, the membrane will be treated to disrupt antibody binding without releasing the target proteins. This approach can be proven to work by repeating the detection of each target protein in sequence, and comparing the signals obtained in the first and second round. Negative controls for specificity of detection are provided for each protein by the antibodies against the other two. Additionally, the membrane will be developed a final time without inclusion of a primary antibody.

If the number of cells available is insufficient, or the abundance of a particular transcription factor is too low, a signal will not be detected. It might be possible to gain greater sensitivity by employing ELISA assays for these proteins, but the greater reliability and specificity of the immunoblot method would be lost. However, neither of these potential problems is likely to be significant. The desired number of cells should routinely constitute only a fraction of each BAL sample. Low abundance of any target protein would be a physiologically relevant result leading to meaningful conclusions. However, it should be noted that the reagents and detection systems available will provide a signal if there is 100-1000 copies of the target protein per cell, which would correspond to not more than 8 femtomoles (0.5-1.5 ng) in the analyzed aliquot.

Characterize tyrosine and serine phosphorylation of STAT-1, IRF-1 and CIITA Changes in transcription factor phosphorylation are often the link from the presence of the factor to its function. This is true even if DNA-binding activity is not directly altered by changes in phosphorylation (David et al., (1995) *Science* 269(5231):1721-3; Wen, Z. et al., (1995) *Cell* 82(2): 241-50; Pine et al., (1994) *Embo J* 13(1): 158-67; Cho et al., (1996) *J Immunol* 157(11): 4781-9; David et al., (1996) *J Biol Chem* 271(27):15862-5; Gupta et al., (1995) *Science* 267(5196):389-93; Hibi et al., (1993) *Genes Dev* 7(11): 2135-48; Parker et al., (1996) *Mol Cell Biol* 16(2): 694-703; Schindler et al., (1992) *Science* 257(5071): 809-13; Shuai et al., (1992) *Science* 258(5089): 1808-12). As described above, both tyrosine and serine phosphorylation of STAT-1 are regulated and control its activity. IRF-1 is a phosphoprotein, but naturally occurring changes in phosphorylation have not been documented, and phosphorylation of CIITA has been little studied. The experiments described here will provide data on the in vivo regulation of STAT-1 by examining the extracts from PBMC and BAL cells for phosphorylation events previously documented primarily in cell-culture systems. The data obtained on IRF-1 and CIITA will go beyond what has been determined previously.

The most straightforward design for this set of experiments is to quantitatively recover the target proteins from cell extracts by immunoprecipitation, separate the recovered proteins by SDS-PAGE, then detect phosphorylation by immunoblot analysis of the separated proteins. It is well established that commercially available anti-phosphotyrosine antibodies can be used to develop immunoblots and determine the presence and extent of tyrosine phosphorylation, with little or no dependence on the particular target protein. Antibodies against phosphoserine are also commercially available, but it is not certain that they will detect such residues in the intended target proteins. Thus, there is some uncertainty as to the successful application of this approach. In addition to the types of positive and negative controls described above, specific detection of phosphotyrosine or phosphoserine can be shown by including the phosphoarnino acid in solution and observing that signals are not obtained.

Although the proteins denatured by SDS-PAGE are most likely to react with the antiphosphoserine antibodies, it remains possible that ELISA would be a successful alternative if immunoblot detection of serine phosphorylation does not work. In that case, wells would be coated with antibody to the target protein, the protein would be bound, and the detection step would utilize antiphosphoserine primary antibodies obtained from a different species than the source of the antibodies against the target proteins. The controls utilized for the immunoblot would essentially apply as well to an ELISA system.

Another alternative is available for analysis of STAT-1 serine phosphorylation. A specific anti-phosphoSTAT-1 (P-Ser) antibody could be made (see Methods) based on the known position of the serine that is subject to regulated phosphorylation, Ser 727 (Wen, Z. et al., (1995) *Cell* 82(2): 241-50). This is quite likely to succeed, since commercially available antibodies specific for phosphorylated forms of several proteins (New England BioLabs) have been obtained by immunization with the appropriate phosphopeptide followed by purification of the specific antibody by use of protein-a, peptide, and phosphopeptide affinity matrices. A similar approach would be used for this project. Metabolic labeling of cells with $^{32}$P-orthophosphate followed by specific immunoprecipitation of target proteins and phosphoamino acid analysis is not appropriate for this project, since the target proteins could be modified during the culture period necessary for the metabolic labeling, and because the amount of material available is not likely to be sufficient for such an approach. While determination of changes in serine phosphorylation may not be readily achieved for any of the target proteins, the likely significance of that regulated post-translational modification strongly supports making the attempt.

These data will be used to establish the connection between the abundance of these factors and their function in this system. The extent of STAT-1 tyrosine phosphorylation will determine the level of activation and thus set minimum and maximum levels of DNA-binding activity. Changes in serine phosphorylation may modulate the DNA-binding activity and have additional effects on STAT-1 function as described above. It is possible that increased abundance of STAT-1 and basal levels of phosphorylation will be detected. Such a result would imply that the in vivo response overall is similar to the response of cultured cells exposed to INF-γ for a prolonged period and reflects the time course of post-translational modifications (phosphorylation and dephosphorylation) together with de novo synthesis of STAT-1 as molecular responses to INF-γ. Data on changes in IRF-1 or CIITA phosphorylation will serve as additional markers of in vivo molecular responses to INF-γ and will provide a strong rationale for future basic research to determine the functional significance of such changes. Should there be changes in abundance but not phosphorylation, it may be that phosphorylation of these factors is not regulated in this system, or, as is possible for STAT-1, that there was no net change that persisted at the time the samples were obtained. Future studies in other systems would be necessary to distinguish these possibilities.

Measure DNA-binding activity of STAT-1, STAT-4, STAT-5, STAT-6, and IRF-1 Measurement of DNA-binding activities will provide the final data needed to evaluate regulation of the molecular responses to the treatment protocol. Detection and quantitation of the STAT family and IRF-1 transcription factors by electrophoretic mobility shift assay of experimental samples will be accomplished by established procedures. Extracts prepared from cultured cells will be included in these assays as positive controls. Controls for specificity and identification of the factors in question will be provided by performing reactions that include competitor oligonucleotides or antisera. Both nonspecific and specific oligonucleotides or antisera will be used.

In contrast to the synchrony of a cell-culture system, in which the entire population is exposed to an added cytokine starting at the same time and lasting for the same amount of time, cells obtained by BAL or in blood samples will represent the total effect of repeated aerosol INF-γ treatment superimposed on the asynchronous start and duration of exposure of individual cells governed by their trafficking into and out of sites where they are exposed. In cell-culture models, INF-γ activation of STAT-1 DNA-binding activity occurs within minutes. In some cell lines, the activity decays very rapidly. In others, including the monocytic cell lines NB4, U937, and THP-1, it persists for several hours (R. Pine and E. Jackson, unpublished). Since STAT-1 regulates the IRF-1 gene, induction of IRF-1 DNA-binding activity by INF-γ is typically detected only after 1-2 hr, but then persists at least 16 hr. Thus, STAT-1 and IRF-1 DNA-binding activity may be present simultaneously, but it is also possible that only one or the other will be detected.

The results obtained from the experimental samples may reveal that both STAT-1 and IRF-1 DNA-binding activity are present, and thus would indicate that in vivo the net outcome of intermittent doses over several days is equivalent to an intermediate time of exposure in a cell-culture system. This would be distinct from the constitutive activation of STAT factors that has been reported in Bcr/abl-transformed cell lines or PBMC from leukemia patients (Carlesso et al., (1996) J Exp Med 183(3): 811-20; Gouilleux-Gruart et al., (1996) Blood 87(5): 1692-7). Furthermore, such a result would strongly suggest that the full panoply of responses to INF-γ was ongoing at the time the samples were obtained. Alternatively, only STAT-1 or IRF-1 DNA-binding activity might be detected. It seems unlikely that only STAT-1 will be detected, since prolonged induction of IRF-1 is the norm, while STAT-1 activation is typically transient. The presence of IRF-1 DNA-binding activity in the absence of STAT-1 DNA-binding activity would imply that the treatment evoked a response equivalent to those seen in cultured cells after overnight treatment with INF-γ. Physiologically this would be consistent with a situation in which the presence of INF-γ had persisted long enough to evoke biological endpoints such as monocyte to macrophage differentiation or elaboration of a Th1 T-cell response.

Assays of STAT-4, -5, and -6 will provide molecular markers for the response of T cells to IL-2, as well as the presence and function of key Th1 or Th2 cytokines. Numerous recent reports have shown that IL-2 activates STAT-5, IL-12 activates STAT-4, and IL-4 activates STAT-6 (Cho et al., (1996) J lmmunol 157(11): 4781-9; Gilmour et al., (1995) Proc Natl Acad Sci USA 92(23): 10772-6; Schindler et al., (1992) Science 257(5071): 809-13). The data obtained here cannot themselves prove such interpretations, since almost every member of the STAT family is activated by more than one cytokine, and almost every cytokine can activate more than one STAT. Specifically, STAT-4 is also activated by INF-α, STAT-5 is also activated by IL-7, IL-15, prolactin, and growth hormone, and STAT-6 is also activated by IL-13 (Ivashkiv, L. B. (1995) Immunity 3(1): 1-4; Darnell (1996) Recent Prog Horm Res 51:391-403; Cho et al., (1996) J Immunol 157(11): 4781-9). It should also be noted that STAT-1 can be activated by IL-6 and IL-10, as well as INF-γ. However, interpretation of this data would be supported by the analysis of cytokine gene expression described above. Furthermore, the assays of STAT-4, -5, and -6 DNA-binding activity would significantly extend those observations by providing data on intracellular molecular effects that occur in conjunction with a defined cytokine profile.

Methods We will extract mRNA from $10 \times 10^6$ BAL cells using GITC and ultracentrifugation. Since RT-PCR can be performed on such small aliquots of cells, total RNA will be extracted, stored at −70° C., and assayed for gene expression of IRF-1. PCR primers will be based on the published sequences and utilize RT-PCR as described for cytokine genes, and compare transcript intensity to b-actin or GAPDH as a control. As IRF-1 is basally expressed, a quantitative approach to RT-PCR will be needed. Total RNA from BAL cells will be reverse-transcribed using oligo-d(T) and PCR, according to standard methods. First-round PCR will be carried out with 20% of the cDNA using the following oligonucleotides: forward primer 5'_GTCAGGGACTTGGA-CAGGAG-3', and reverse primer 5'-AGCTCGGGGGAAATGTTAGT-3'. IRF-1 expression will be normalized against GAPDH expression.

Preparation of cell extracts Cells from BAL will be processed into RPMI media with no serum, as described above, then counted, then transferred to tissue-culture plates. After 2 hr at 37° C., nonadherent cells will be removed with the media and counted again. The number of adherent cells will be obtained as the difference between the two cell counts. PBMC will be processed into RPMI media with no serum, as described above, then counted. All remaining steps will be carried out at 0-4° C. Cells in suspension will be centrifuged (200×g, 10 min), then the supernatant will be aspirated and the pellet resuspended in phosphate-buffered saline (PBS). This step will be repeated, then these cells will be centrifuged once more, and the final PBS supernatant will be aspirated. Attached cell monolayers will be washed by adding then aspirating PBS. PBS will be added again and the monolayers will be detached by scraping. The cells and PBS will be transferred to centrifuge tubes and centrifuged, and then the PBS will be removed by aspiration. Washed cell pellets will be lysed by suspending them in lysis buffer (20 mM Hepes-Na, pH 7.9, 0.1 mM EDTA-Na, 0.1 M NaCl, 0.5% NP-40, 10% glycerol, 1 mM DTT, 0.4 mM PMSF, 3 μg/ml aprotinin, 2 μg/ml leupeptin, 1 μg/ml pepstatin, 100 μM $Na_3VO_4$, 10 mM $Na_2P_2O_7$, 5 mM NaF) (3 μl per $10^5$ cells) and incubating them for 5 min. Nuclei will be recovered by centrifugation (500×g, 10 min). The supernatant will be removed, then clarified by centrifugation (13,000×g, 15 min). The resulting supernatant will be recovered as the cytoplasmic extract, frozen in crushed dry ice or liquid nitrogen, then stored at −80° C. The nuclear pellet will be resuspended in wash buffer (lysis buffer without NP-40), then recovered by centrifugation. The supernatant will be aspirated, then the pellet will be suspended in extraction buffer (wash buffer, except 0.3 M NaCl instead of 0.1 M) (3 μl per $10^5$ cells) and mixed for 30 min. The extracted nuclei will be pelleted by centrifugation and the supernatant recovered as the nuclear extract, which will be frozen and stored as above. Protein concentrations will be measured so that comparable amount of different extracts can be used in an experiment. This usually entails using the same volume of each extract, since the use of a fixed ratio of extraction buffer volume to cell number typically yields uniform protein concentrations for nuclear or cytoplasmic extracts within a single set of extracts and from different preparations.

Immunochemical procedures Immunoblots will be performed as follows: Extracts and protein size standards will be mixed with concentrated Laemmli sample loading buffer for SDS-PAGE, and applied to a discontinuous Tris-glycine gel system prepared with an 8% separating gel and a 4% stacking gel according to standard protocols. This gel percentage will resolve all the proteins of interest. Electrophoresis will be performed at constant voltage until the marker dye reaches the bottom of the gel. The gel will be equilibrated in transfer buffer (Tris-glycine plus 15% methanol), and then proteins will be transferred with the same buffer to nitrocellulose membrane using a semidry apparatus (BioRad Transblot, SD). Membranes will be developed by standard procedures. Briefly, this will entail blocking by incubation with nonfat dry milk in Tris-buffered saline plus Tween 20 detergent, incubating with a specific primary antibody, washing several times in blocking solution, incubating with an enzyme-linked second antibody, washing in buffer without blocking agent, and incubating with an enzyme substrate. For chemiluminescent substrates, signal will be detected with X-ray film. Alternatively, a Molecular Dynamics Storm 860 instrument is available at PHRI for detection of signal from chemifluorescent substrates. Based on the experimental design, the optimal conditions for transfer of STAT-1 and IRF-1, which were previously determined to be essentially the same (Pine et al., (1994) *Embo J* 13(1): 158-67; Pine et al., (1990) *Mol Cell Biol* 10(6): 2448-57; Pine unpublished), will be used for this project, as will the previously determined optimal development conditions for each of those proteins. For CIITA, optimal detection conditions, including the choice of blocking agent, detergent concentration, time of incubation for each step, and detection method will be empirically determined with control extracts prepared from cultured cells. Immunoprecipitation of STAT-1 and IRF-1 will be performed as previously described, with minor modifications. Specifically, the use of *S. aureus* cells for recovery of IRF-1 bound to anti-IRF-1 antibodies has been replaced by the use of protein-a agarose.

Should an ELISA assay be desired for detection of transcription factor abundance or to examine phosphorylation, detailed methods based on standard procedures will be developed empirically with the use of control extracts from cultured cells. To increase sensitivity, the preferred approach will entail binding of a capture antibody to the wells of a microtiter dish, followed by blocking, then incubation with the desired extract. After further washing, the second specific antibody would be used, and then the enzyme-linked antibody against the secondary antibody would be used, and the substrate incubation performed. Washes would be included after each antibody incubation. For STAT-1, it will be possible to use rabbit polyclonal antiserum to provide capture antibodies and mouse monoclonal antibodies for detection, or vice versa, since both are available for the protein and for phosphotyrosine or phosphoserine. For IRF-1 and CIITA, only rabbit polyclonal antibodies against the protein are available, so it will be necessary to use mouse monoclonal antibodies against phosphotyrosine or phosphoserine. Detection of those proteins will require that the extract be used to coat the wells of the microtiter dish, followed by incubation with specific primary antibody and enzyme-linked secondary antibody. Controls for specificity in assays of experimental samples will include omission of primary antisera and/or inclusion of phosphoamino acids, as appropriate.

Electrophoretic mobility shift assays Optimal assays have been developed for each of the indicated STAT family members and for IRF-1 (Pine and Gilmour, supra). Reactions will include nonspecific and specific competitors, or nonspecific and specific antibodies. Each reaction will be done with 5 µg of extract protein, which is typically 2-3 µl. For reactions with competitors, those oligonucleotides will be included with the radiolabeled probe when it is mixed with the extracts. For reactions with antibodies, the protein-DNA-binding reactions will be carried out as usual, then antiserum will be added and the incubation continued. When incubations are completed, reactions will be applied to native polyacrylamide gels, which will then be electrophoresed at 4° C. After the gels are dried, the results will be obtained by autoradiography, or with a Molecular Dynamic PhosphoImager.

We will compare data obtained at baseline and after r INF-γ treatment by Student's paired t test and express analysis as mean±SEM. Based on previous studies, we will need to detect a 0.3 L difference in FEV1 and a difference of $3 \times 10^5$ cells/ml. With 30 subjects, we will have a power of 80%. Thus we will recruit 15 subjects for each group.

Subject Population Medical evaluations will be performed on 400 individuals with asthma. Thirty patients with mild-moderate persistent allergic asthma will be randomized to receive INF-γ aerosol (n=15) versus standard treatment (n=15). Patients must have pulmonary function and bronchial provocation measurements. There must be no contraindication to fiber optic bronchoscopy. The majority of the study population will be recruited from the Bellevue Hospital Primary Care Asthma Clinic. The demographic characteristics of our patient population are: 90% minorities (mainly Hispanic and African American), aged 18-79 (median=39), and have a 1:2 male:female ratio.

Potential Risks In general, the risk and severity of side effects to interferon-γ (INF-γ) are related to the amount of medication given. At the dose used in this study (50 mcg/m$^2$), most common possible side effects include fever, headache and malaise. Occasional nausea and vomiting have been reported at high doses. Aerosolization has not been associated with adverse reactions, although headache, cough and fever may be expected. In the event of severe symptoms, medication will be stopped. There is a risk of previously unknown side effects of INF-γ not related to asthma. An individual may develop an allergic reaction to the protein portion of INF-γ, in which case it will be discontinued.

Risk Management Procedures To minimize any risks, bronchoalveolar lavage is performed after medical evaluation excluding individuals with cardiac disease or history of angina. Chest x-ray and blood studies including bleeding parameters are performed. Bronchoalveolar lavage will be performed by pulmonary fellows under faculty supervision. Following the procedure, the study subjects will remain NPO for 3 hr and vital signs will be taken every 30 min for 3 hr. All patients will have cardiac monitoring during the procedure and will receive nasal $O_2$ during and after the procedure for 2 hr to prevent any hypoxemia. All patient data will be kept locked in the pulmonary research offices. In the event of adverse effects to subjects, a "crash cart" is kept with the fiber optic bronchoscope, including endotracheal tubes, injectable lidocaine and epinephrine, etc, and all procedures are done in the hospital with house staff and a CPR team on call. All of the bronchoalveolar lavage procedures will be periodically reviewed to identify any increased incidence of untoward effects and identify their cause.

Example 13

Figure 12:
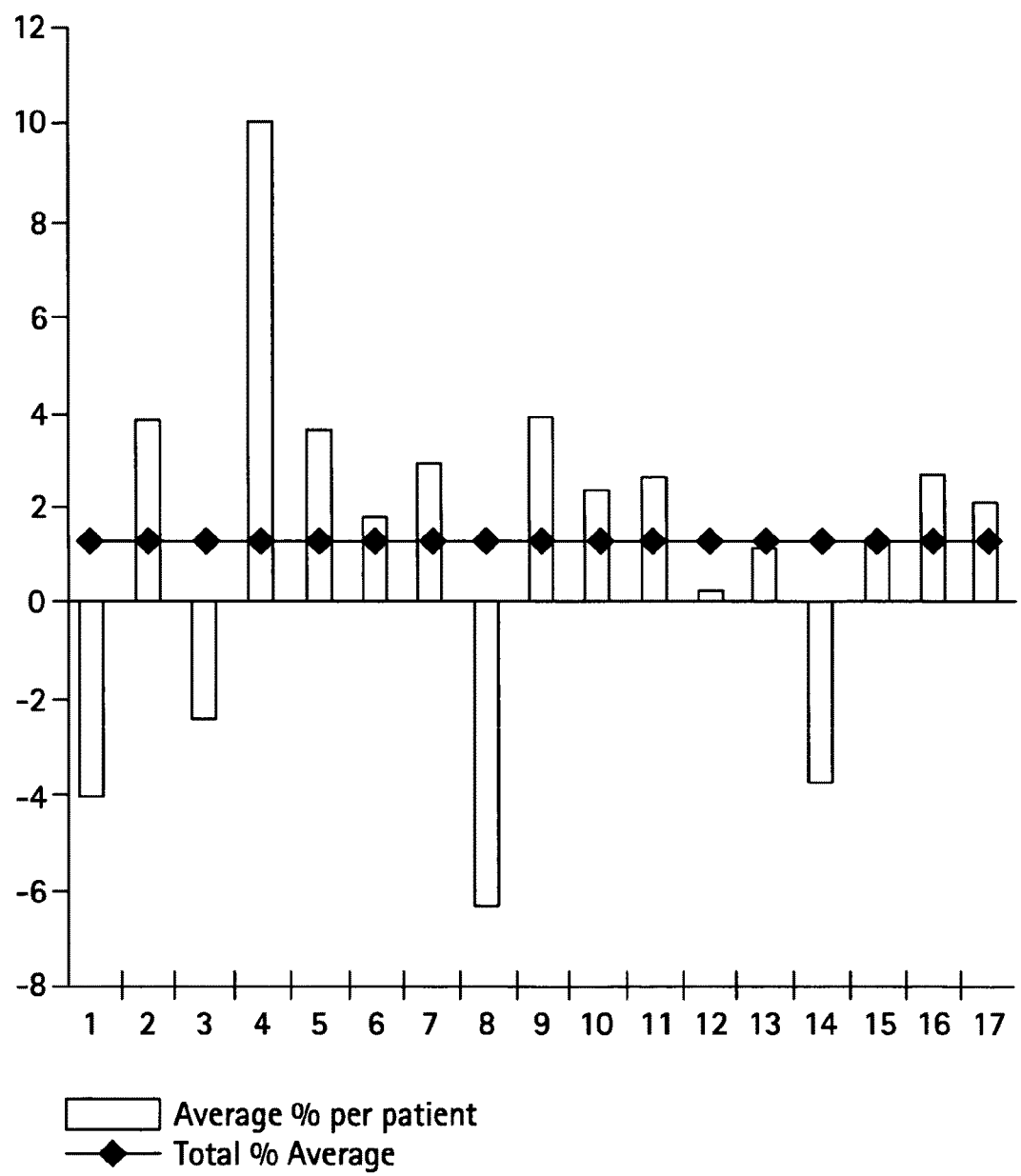
FIG. 12 provides a summary of the percent change in peak flow measurements referred to in FIG. 2. The average peak flow increased after aerosol interferon γ, with significant increases in a few patients. Of note, in all patients where peak flow measurements decreased after interferon γ, none developed cough or other complaints. These data indicate that aerosol interferon γ is safe and well tolerated in patients with airway disease.

All patients receiving aerosol interferon-γ were studied with spirometry to assess reversible airways disease. Most patients had chronic obstructive airways disease (COPD) without signs of reversibility. At each aerosol treatment, patients underwent monitoring of peak flows before and after each treatment. Data for all patients is shown in FIG. 11. Summary data of percent change in peak flow measurements is shown in FIG. 12. The average peak flow increased after aerosol interferon-γ, with significant increases in some patients. These data demonstrate that aerosol interferon-γ is safe and well tolerated in patients with chronic obstructive airways disease (COPD).

Example 14

Bronchoscopy

Bronchoscopy with bronchoalveolar lavage (BAL) was performed at baseline and after six months of treatment on the patient population of Example 13 to evaluate the levels of certain pro-fibrotic and inflammatory cytokines. An optional bronchoscopy may be performed at the completion of treatment. Bronchoscopy with BAL was generally performed in a day surgery setting. However, some subjects may be admitted overnight if observation is warranted. The procedure is performed as follows.

Each study patient was evaluated for bronchoscopy as per hospital protocol. Each evaluation includes measuring Hgb, platelets, BUN/CR, coagulation panel, ABG with $PO_2 \geq 65$ mmHg, EKG, and chest x-ray.

Contraindications to bronchoscopy include lack of patient cooperation, recent myocardial infarction, malignant arrhythmias, refractory hypoxemia, unstable bronchial asthma, partial tracheal obstruction or vocal cord paralysis, bleeding diathesis and uremia. Patients must be NPO at least 8 hours prior to bronchoscopy. An intravenous line was placed, supplemental oxygen was administered and continuous pulse oximetry and blood pressure monitoring was performed. Liquid and viscous lidocaine, a topical anesthetic, was used in the nasal passage and posterior pharynx for passage of the bronchoscope. During the procedure midazolam and/or fentanyl may be administered to cause sedation and decrease of the cough reflex. These medications are routinely used in bronchoscopy. The bronchoscope was passed through the nose and vocal cords, and an endobronchial exam was performed.

BAL was then performed in one or more segments of the lung by administering 50 ml aliquots of sterile normal saline, for a total of up to 300 ml, and applying gentle suction for maximum return of fluid. The BAL fluid was processed as follows. After BAL fluid was obtained from the patient, it was processed in the laboratory under the standardized protocol used for processing all BAL. The BAL fluid was filtered through a sterile gauze. A total cell count with differential was performed in a hemocytometer. Cell viability was determined by the Trypan Blue method. Ten cytocentrifuge slides were prepared from each lobe of BAL fluid and frozen at −70° C. 24 hour supernatants were collected at a concentration of $10^6$ cells/ml for cytokine ELISA assays. The volume of epithelial lining fluid was determined according to the protein method. Following centrifugation, BAL fluid supernatant was concentrated 10× to 50× using the AMICON filter method. Cytokine assays were performed with Luminex systems (Minneapolis, Minn.). Luminex MAP, facilitates the simultaneous evaluation of multiple immune mediators with advantages of higher throughput, smaller sample volume, and lower cost. It is a valid alternative method to ELISA for the evaluation of the majority of cytokines and for the characterization of immune system status. Cytokines were analyzed using the Luminex system including Inteferon-gamma IL-8 and TGF-beta. All samples were assayed in triplicate.

Each patient was monitored for potential side effects of bronchoscopy, including, but not limited to: fever, shortness of breath, hemoptysis and pneumothorax for 4 hours post procedure in the GCRC by the clinical nursing staff.

Example 15

Ten IPF patients treated with INF-γ were followed for a period of 30 weeks, nine IPF patients were followed for a period of 40 weeks, and six IPF patients were followed for a period of fifty weeks. The characteristics of the patients in the treatment group are provided in Table 3. Forced Vital Capacity (FVC) was measured by standard techniques of pulmonary medicine. The results are demonstrated in FIG. 16. The patients as a group demonstrated an actual improvement in FVC in the single digit percentage range over the time monitored. This indicates that INF-γ may not only stabilize what is considered a gradually progressive condition but actually reverse some of the pulmonary deterioration. IPF patients undergoing no treatment as represented by the NYU Control Group of nine patients experienced a gradual deterioration of pulmonary function exemplified by a reduction in FVC also in the single digit percentage range over the same 30, 40 and 50 week time period. The characteristics of the patients in the NYU Control Group are also provided in Table 3.

These INF-γ treatment and NYU Control groups were then compared to studies performed by others using other treatments with IPF patients and providing other control groups. The characteristics of the patients in each group are also provided in Table 3. Again, a graphic display of the deterioration in FVC over time is presented in FIG. 16. The patients receiving acetyl cysteine and the control group to which they are compared are described by Demedts et al., *N Engl J Med* 2005; 353:21, hereby incorporated by reference. Patients receiving acetyl cysteine are identified as acetyl cysteine Tx, and patients from the control group of this study are identified as acetyl cysteine control in FIG. 16. The patients receiving etanercept and the control group to which they are compared are described by Raghu et al., *Am J Resp Crit Care Med* 2008; 178: 948-955, hereby incorporated by reference. Patients receiving etanercept are identified as etanercept Tx, and patients from the control group of this study are identified as etanercept placebo in FIG. 16. Further, Intermune, Burlingame, Calif. conducted studies on IPF patients using perfenadone as treatment. The results are generally available from Intermune, Brisbane, Calif. and from internal communications at the company. In a first study involving 344 patients receiving 2403 mg perfenadone over 72 weeks, at the end there was a 6.49% reduction in the FVC on average for patients receiving treatment versus a 7.23% reduction in the FVC on average for patients receiving placebo over the 72 week period. These data are presented in FIG. 16 as Capacity 1 PFD and Capacity 1 Placebo, respectively. In a second study involving 435 patients receiving 2403 mg perfenadone over 72 weeks, at the end there was a 6.49% reduction in the FVC on average for patients receiving treatment versus a 9.55% reduction in the FVC on average for patients receiving placebo over the 72 week period. These data are presented in FIG. 16 as Capacity 2 PFD and Capacity 2 Placebo, respectively.

The results provided in FIG. 16 demonstrate that patients suffering from IPF experience not only arrest of further deterioration but actual improved pulmonary function as demonstrated by increased FVC over time. To the contrary, patients receiving acetyl cysteine, etanercept, perfenadone or no treatment whatsoever demonstrate continued deterioration of pulmonary function as evidenced by decreased FVC over time.

TABLE 3

DEMOGRAPHICS

| Group | N | Mean Age | Gender M | Gender F | % FVC at Baseline | % DLCO at Baseline |
|---|---|---|---|---|---|---|
| INF Patients | 10 | 69.3 ± 6.1 | 8 | 2 | 79.1 ± 13.4 | 47.7 ± 9.03 |
| NYU Placebo | 9 | 71.1 ± 9.4 | 6 | 3 | 74.2 ± 19.3 | 49.4 ± 18.7 |
| Acetylcysteine Tx | 80 | 62.0 ± 9.0 | 55 | 25 | 64.8 ± 15.4 | 43.0 ± 13.1 |
| Acetylcysteine Placebo | 75 | 64.0 ± 9.0 | 60 | 15 | 66.6 ± 14.2 | 44.8 ± 15.2 |
| Etanercept Tx | 46 | 65.2 ± 7.7 | 35 | 11 | 62.2 ± 11.9 | 36.3 ± 12.6 |
| Etanercept Placebo | 41 | 65.1 ± 7.1 | 24 | 17 | 61.1 ± 12.7 | 36.9 ± 10.8 |
| Intermune PFD Capacity 1 Tx | 171 | 67 | 125 | 46 | 74.5 | |
| Intermune PFD Capacity 1 Placebo | 173 | 67 | 125 | 48 | 70.3 | |
| Intermune PFD Capacity 2 Tx | 174 | 66 | 118 | 56 | 73 | |
| Intermune PFD Capacity 2 Placebo | 174 | 67 | 129 | 45 | 73.6 | |
| Intermune PFD Capacity 2 Placebo | 174 | 67 | 129 | 45 | 73.6 | |

FIG. 13 provides the levels of interferon-γ measured in the BAL fluid of six of the ten patients both before and after treatment with aerosolized interferon-γ. FIG. 14 depicts the amount of TGF-β protein measured in BAL fluid from six IPF patients treated with aerosol interferon gamma. Pre—refers to baseline bronchoscopy and post is after a minimum of 24 weeks of treatment. Units are picograms of TGF-β per ml of BAL fluid. FIG. 14 provides the levels of IL-8 measured in the BAL fluid of six patients both before and after treatment with aerosolized interferon-γ.

Example 16

Ten patients were administered 100 μg of recombinant INF-γ by oral nebulizer. The patients were then examined to determine the percentage of recombinant INF-γ that was deposited in various body compartments. Delivery to the lungs was assessed via radiolabeled gamma camera studies. The results are provided in Table 4. The first column provides the percentage of the amount of INF-γ that was deposited in the middle lobe of the lung compared to that deposited in the lung total. The second column expresses the percentage of the entire dose that was deposited in the middle lobe of the lung. The third column expresses the percentage of the entire dose that was deposited in the lung total. The fourth column expresses the percentage of the entire dose that was deposited in the stomach. The fifth column expresses the exhaled activity. The sixth column expresses the ratio of the amount of the entire dose that was deposited in the central lung compared to the amount of the entire dose that was deposited in the peripheral lung. The seventh column expresses the ratio of the amount of the entire dose that was deposited in the central lung compared to the amount of the entire dose that was deposited in the peripheral lung in relation to how xenon deposits in the lung by ratio of central to peripheral deposition. The eighth column expresses the percentage of the entire dose that remained in the drug cup of the nebulizer.

TABLE 4

| Patient | ML % of Total Lung CTs | % ML Depo | % Lung Deposition* | % Stomach Deposition* | % Exhaled Activity*† | aC/P deposition | sC/P deposition | % Left in drug cup | MMAD |
|---|---|---|---|---|---|---|---|---|---|
| 1 | 32.97 | 15.86 | 48.1 | 26.7 | -5.4 | 1.16 | 1.31 | 24 | NA |
| 2 | 25.89 | 14.01 | 54.1 | 10.1 | 2.4 | 0.85 | 1.10 | 21 | 1.9 |
| 3 | 28.70 | 18.65 | 65.0 | 2.0 | 11.6 | 0.64 | 0.88 | 16 | 1.8 |
| 4 | 27.31 | 17.59 | 64.4 | 2.5 | -3.0 | 0.84 | 1.16 | 18 | 1.8 |
| 5 | 23.00 | 10.74 | 46.7 | 21.7 | -2.0 | 0.82 | 1.17 | 16 | 2.0 |
| 6 | 29.00 | 15.74 | 54.3 | 1.1 | 0.3 | 0.83 | 1.22 | 27 | 2.1 |
| 7 | | | 33.3 | 23.7 | 5.4 | 0.78 | 1.13 | 28 | 1.3 |
| 8 | | | 48.0 | 6.0 | 7.3 | 0.75 | 1.21 | 26 | 1.3 |
| 9 | 26.3 | 17.02 | 64.7 | 6.5 | -5.9 | 0.85 | 1.42 | 28 | 1.2 |
| 10 | | | 26.0 | 8.0 | 26.9 | 0.88 | 1.37 | 23 | 1.3 |
| 10 repeat | | | 34.8 | 8.6 | 9.3 | 0.85 | 1.35 | 40 | 1.3 |

*Data expressed as percent of nebulizable activity

†Exhaled activity - Amount nebulized‡ − (Total deposition by AC + 1-neb base activity + mouthpiece activity)

‡Amount nebulized = Initial nebulizer charge − post chamber activity

We claim:

1. A method for treating a pulmonary disease in a subject suffering from a pulmonary disease, comprising administering 10-1000 μg of an aerosolized INF-γ sufficient to provide a therapeutically effective amount to parenchymal tissue of the lungs of the subject.

2. The method of claim 1 wherein the pulmonary disease is idiopathic pulmonary fibrosis.

3. The method of claim 1 wherein the pulmonary disease is mixed connective tissue disease.

4. The method of claim 1, wherein the pulmonary disease improves so that a patient demonstrates an increase of at least 2% of predicted FVC relative to values from placebo.

5. The method of claim 1, wherein INF-γ is administered in a dose and in a manner sufficient to transmit the INF-γ so that amounts of at least 100 picograms/milliliter of the INF-γ may be measured in the bronchoalveolar lavage (BAL) fluid of the subject.

6. The method of claim 1, wherein INF-γ is administered in a dose and in a manner sufficient to transmit the INF-γ so that amounts of at least 150 picograms/milliliter of the INF-γ may be measured in the bronchoalveolar lavage (BAL) fluid of the subject.

7. The method of claim 1, wherein aerosolized INF-γ is administered at a dose ranging from about 100 to 750 μg at least three times per week.

8. The method of claim 1, wherein aerosolized INF-γ is administered at a dose of about 100 μg three times per week.

9. The method of claim 1, wherein said administering results in deposition of INF-γ in the lungs of patients with pulmonary disease.

10. The method of claim 1, wherein said administering results in deposition of about 40% of the INF-γ in lungs of patients with pulmonary disease.

11. The method of claim 1, wherein said administering results in deposition of about 15% of the INF-γ in a middle lobe of lungs of patients with pulmonary disease.

12. The method of claim 1, wherein said administering results in deposition of about 60% of the INF-γ in lungs of patients with pulmonary disease.

13. The method of claim 1, wherein INF-γ is administered in a dose and in a manner sufficient to provide a measurable decrease in the level of IL-8 present in the bronchoalveolar lavage (BAL) fluid of a patient.

14. The method of claim 1, wherein INF-γ is administered in a dose and in a manner sufficient to provide at least a 10% decrease in the level of IL-8 present in the bronchoalveolar lavage (BAL) fluid of a patient.

15. The method of claim 1, wherein INF-γ is administered in a dose and in a manner sufficient to provide at least a 20% decrease in the level of IL-8 present in the bronchoalveolar lavage (BAL) fluid of a patient.

16. The method of claim 1, wherein INF-γ is administered in a dose and in a manner sufficient that the level of IL-8 in the BAL fluid of a patient suffering from a pulmonary disease is reduced to an amount no more than 50% more than the level of IL-8 in the BAL fluid of a normal control substantially free of a pulmonary disease.

17. The method of claim 1, wherein INF-γ is administered in a dose and in a manner sufficient to produce at least a 10% increase in the level of TGF-β present in the BAL fluid of a patient.

18. The method of claim 1, wherein INF-γ is administered in a dose and manner and with a nebulizer chosen so as to provide delivery of at least about 60% of the INF-γ to the lungs of the subject.

19. A method of treating a subject having a pulmonary disease comprising delivering 10-1000 μg of an aerosolized INF-γ sufficient to provide a therapeutically effective amount to parenchymal tissue of the lungs of the subject in combination with a therapeutically effective amount of an immunosuppressive or anti-inflammatory agent.

20. The method of claim 19, wherein the immunosuppressive or anti-inflammatory agent is selected from the group consisting of a corticosteroid, azathioprine and cyclophosphamide.

* * * * *